(12) United States Patent
Leonardi et al.

(10) Patent No.: US 10,611,532 B2
(45) Date of Patent: Apr. 7, 2020

(54) CONTAINER CLOSURE OPERATED BY ROTATION

(71) Applicant: BRACCO IMAGING SPA, Milan (IT)

(72) Inventors: Marco Leonardi, Gorgonzola (IT); Cristina Neira, Turin (IT); Andrea Romeo, Milan (IT); Marta Palenzona, Pozzolo Formigaro (IT)

(73) Assignee: BRACCO IMAGING SPA, Milan (IT)

( * ) Notice: Subject to any disclaimer, the term of this patent is extended or adjusted under 35 U.S.C. 154(b) by 0 days.

(21) Appl. No.: 16/474,838

(22) PCT Filed: Dec. 18, 2017

(86) PCT No.: PCT/EP2017/083265
§ 371 (c)(1),
(2) Date: Jun. 28, 2019

(87) PCT Pub. No.: WO2018/122018
PCT Pub. Date: Jul. 5, 2018

(65) Prior Publication Data
US 2019/0329944 A1    Oct. 31, 2019

(30) Foreign Application Priority Data

Dec. 29, 2016 (EP) .................................... 16207411

(51) Int. Cl.
*B65D 47/24* (2006.01)
*A61M 39/22* (2006.01)
*B65D 47/36* (2006.01)

(52) U.S. Cl.
CPC ........... *B65D 47/244* (2013.01); *A61M 39/22* (2013.01); *B65D 47/36* (2013.01)

(58) Field of Classification Search
CPC ....... B65D 47/244; B65D 47/36; A61M 39/22
(Continued)

(56) References Cited

U.S. PATENT DOCUMENTS 4,432,760 A * 2/1984 Mittleman ............... A61M 5/36
137/906
5,421,487 A * 6/1995 Moretti ................ B65D 47/242
222/153.1
(Continued)

FOREIGN PATENT DOCUMENTS

JP     H08244822 A    9/1996
WO    1998034582 A1  8/1998

OTHER PUBLICATIONS

PCT Search Report and Written Opinion for PCT/EP2017/083265, dated Apr. 4, 2018.

*Primary Examiner* — James N Smalley
(74) *Attorney, Agent, or Firm* — Vivicar Law, PLLC

(57) ABSTRACT

A solution is proposed for closing a mouth (125) of a container (110) of a liquid (105). A corresponding closure (135) comprises a cap (205) having fixing means (318) for fixing the cap (205) to the container (110), the cap (205) being rotatable around a longitudinal axis (203) of the container (110) in a fixed condition wherein the closure (135) is fixed to the container (110), a delivery port (336) for delivering the liquid (105) from the container (110), a cap suction conduit (345) for suctioning air into the container (110) during the delivering of the liquid (105) and a connector (342) for connecting a delivery device (805) of the liquid (105), the connector (342) being in fluid communication with the delivery port (336), a cursor (210) having a thread (406) for screwing the cursor (205) with respect to the container (110), a valve member (424) in a closed position wherein the valve member (215) closes the delivery port (336), and a cursor suction conduit (433) slidebly coupled with the cap suction conduit (345), a frangible element (351) closing the cap suction conduit (345) or the cursor suction conduit (433), and dragging means (327, 409) for dragging the cursor (210) into rotation by the cap (205), wherein the
(Continued)

closure (135) is configured to cause the cursor (210) to slide with respect to the cap (205) in response to at least one rotation of the cap (205) thereby moving the cursor suction conduit (433) to break the frangible element (351), putting in fluid communication the cursor suction conduit (433) with the cap suction conduit (345), and moving the valve member (424) to an open position, wherein the valve member (215) opens the delivery port (336).

15 Claims, 13 Drawing Sheets

(58) Field of Classification Search
USPC .................................. 215/309; 222/519–521
See application file for complete search history.

(56) References Cited

U.S. PATENT DOCUMENTS

| | | | |
|---|---|---|---|
| 5,431,305 A * | 7/1995 | Kaminski | B65D 47/244 |
| | | | 222/109 |
| 5,713,493 A | 2/1998 | Garibaldi | |
| 5,848,994 A | 12/1998 | Richmond | |
| 6,571,994 B1 * | 6/2003 | Adams | B65D 47/244 |
| | | | 222/521 |
| 2003/0127467 A1 | 7/2003 | Adams et al. | |
| 2005/0236440 A1 * | 10/2005 | Cho | B65D 47/244 |
| | | | 222/519 |
| 2011/0168292 A1 | 7/2011 | Luzbetak et al. | |

\* cited by examiner

CONTAINER CLOSURE OPERATED BY ROTATION

CROSS-REFERENCE TO RELATED APPLICATIONS

This application is the national stage application of corresponding international application number PCT/EP2017/083265, filed Dec. 18, 2017, which claims priority to and the benefit of European application no. 16207411.6, filed Dec. 29, 2016, all of which are hereby incorporated by reference in their entirety.

TECHNICAL FIELD

The present disclosure relates to the field of containers for liquids. More specifically, the disclosure relates to closures for these containers.

BACKGROUND ART

The background of the present disclosure is hereinafter introduced with the discussion of techniques relating to its context. However, even when this discussion refers to documents, acts, artifacts and the like, it does not suggest or represent that the discussed techniques are part of the prior art or are common general knowledge in the field relevant to the present disclosure.

Containers of impervious material (for example, glass) are commonly used to store liquids in a number of applications. Particularly, in medical applications the containers store medical liquids to be administered to patients; for example, in hospital environments these containers are commonplace for storing contrast agents that are to be injected into the patients (such as by an automated injection system during scan examinations thereof).

Most containers have a mouth (i.e., an opening) for loading and delivering the liquid; a typical example is a bottle, i.e., a rigid container having a larger body with a neck ending with the mouth. Each container of this type is provided with a closure, which closes the container to avoid losing the liquid and to protect the liquid from environment contamination (before its use).

A widespread type of closure is based on a membrane that seals the mouth of the container. In this case, a spike (for example, a needle) is commonly used to pierce the membrane for extracting the liquid from the container through it (with the container that remains substantially closed even when the spike is removed after the administration of the liquid). However, any accidental contacts with the spike may contaminate it and then the liquid when the spike is inserted into the container, with a consequent final possible contamination of the patient. Moreover, the spike is quite hazardous and it may cause injuries to a corresponding operator, with the risk of transmitting diseases as well.

Alternatively, the closure may be provided with an internal spike (which is not accessible from the outside). In this case, when a delivery device is coupled with the closure (for example, by screwing a luer lock fitting), the delivery device pushes the spike that pierces the membrane analogously to the previous technique.

In any case, the piercing of the membrane by the spike (either internally or externally to the closure) may cause the detachment of particles of the membrane and their falling within the container, with the risk of contamination of the liquid stored in the container.

Closures that do not require any spike for delivering the liquid (i.e., of the spike-less type) have also been proposed. For example, a closure of this type may be provided with a valve member that closes a delivery port of the liquid. When the delivery device is coupled with the closure of the container, the delivery device pushes the valve member inwards the container, thereby opening the delivery port that allows the liquid to flow from the container to the delivery device. The delivery port of the closure may also be sealed by a frangible element, which is broken by the valve member when it opens the delivery port.

Moreover, the closure may be provided with an elastic element associated with the valve member. According to this technique, the delivery device pushes the valve member to open the delivery port in opposition to the elastic element; therefore, when the delivery device is removed (after the administration of the liquid) the elastic element moves back the valve member so as to close the delivery port again.

In addition, as mentioned in WO-A-98/34582, the closure may have an air release valve to allow air to flow into the container as the liquid is delivered. As described in US-A-2011/0168292, the closure may also have one or more air-release openings, or vents, which are provided with an umbrella valve, with a long tube and a short tube or with a self-sealing valve; the air-release openings are sealed by a microhole covering, which is a semi-permeable membrane that allows air to enter or to exit but it does not permit the passage of liquids.

However, none of the closures known in the art is completely satisfactory under several points of view. For example, improvements would be desirable with respect to structure, assembling, usage and safety of the closures.

SUMMARY

A simplified summary of the present disclosure is herein presented in order to provide a basic understanding thereof; however, the sole purpose of this summary is to introduce some concepts of the disclosure in a simplified form as a prelude to its following more detailed description, and it is not to be interpreted as an identification of its key elements nor as a delineation of its scope.

In general terms, the present disclosure is based on the idea of providing a valve member closing a delivery port for delivering a liquid from a container and a frangible element closing a suction conduit for suctioning air into the container.

Particularly, an aspect provides a closure (for closing a mouth of a container of a liquid) that comprises a valve member closing a delivery port for delivering the liquid and a frangible element closing a suction conduit for suctioning air into the container, wherein the closure is rotatable to cause a cursor to slide (in response to at least one rotation) thereby moving a suction conduit of the cursor to break the frangible element and moving the valve member of the cursor to open the delivery port.

A further aspect provides a product containing this closure.

A further aspect provides a method for assembling the closure.

A further aspect provides a method for manufacturing the product.

A further aspect provides a method for using the product.

More specifically, one or more aspects of the present disclosure are set out in the independent claims and advantageous features thereof are set out in the dependent claims, with the wording of all the claims that is herein incorporated verbatim by reference (with any advantageous feature provided with reference to any specific aspect that applies mutatis mutandis to every other aspect).

BRIEF DESCRIPTION OF THE DRAWINGS

The solution of the present disclosure, as well as further features and the advantages thereof, will be best understood with reference to the following detailed description thereof, given purely by way of a non-restrictive indication, to be read in conjunction with the accompanying drawings (wherein, for the sake of simplicity, corresponding elements are denoted with equal or similar references and their explanation is not repeated, and the name of each entity is generally used to denote both its type and its attributes—such as value, content and representation). In this respect, it is expressly intended that the figures are not necessary drawn to scale (with some details that may be exaggerated and/or simplified) and that, unless otherwise indicated, they are merely used to illustrate the structures and procedures described herein conceptually. Particularly.

DETAILED DESCRIPTION

Figure 1:
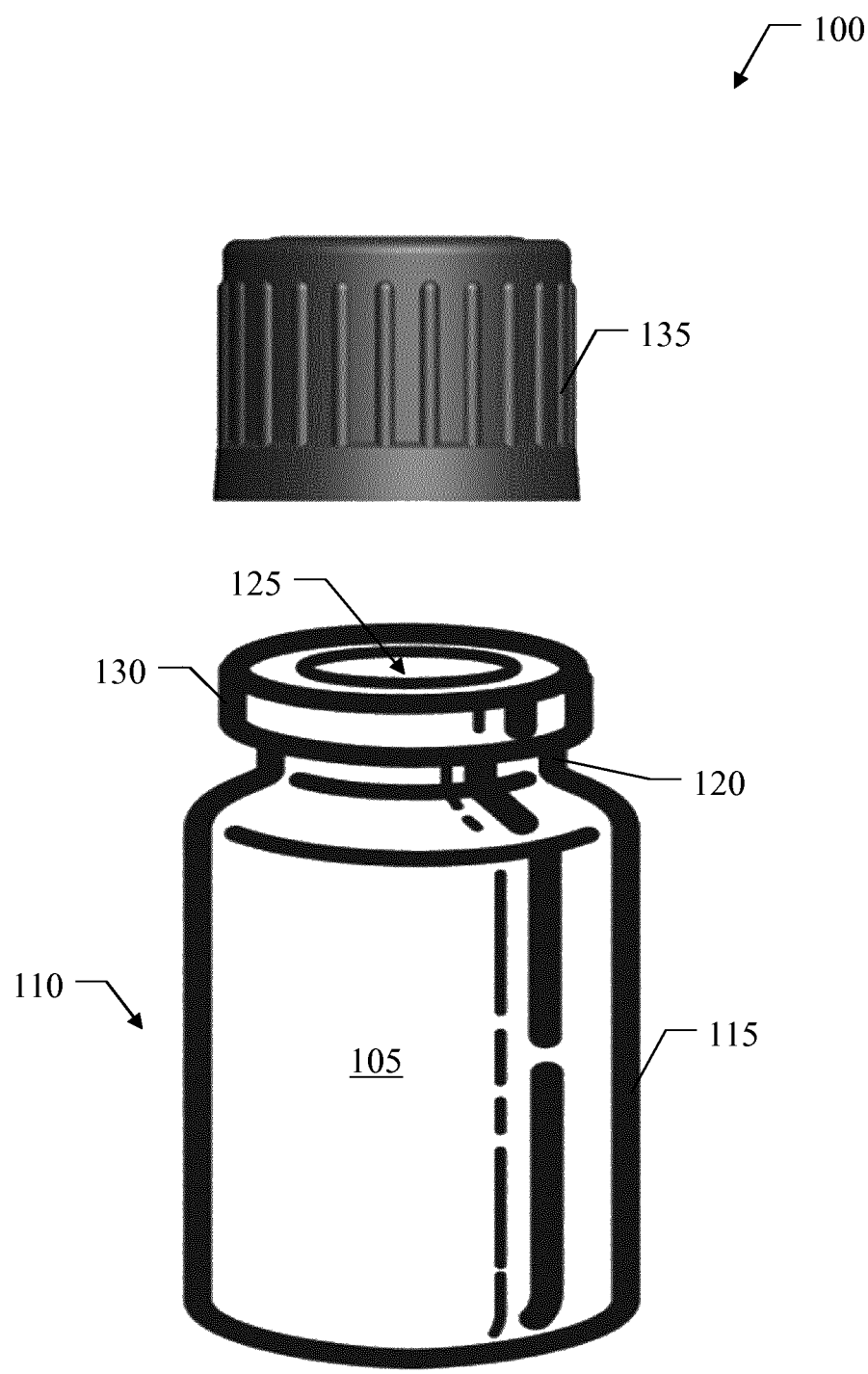
FIG. 1 shows a schematic expanded view of a medical product wherein the solution according to an embodiment of the present disclosure may be applied.

With reference in particular to FIG. 1, a schematic exploded view is shown of a medical product 100 wherein the solution according to an embodiment of the present disclosure may be applied.

The medical product 100 is an artifact for use in medical applications (for example, in hospitals). The medical product 100 contains a medical liquid 105 to be administered to a patient, for example, a contrast agent (such as ISOVUE by Bracco Diagnostics Inc., trademarks) to be injected into the patient by an (automated) injection system during a scan examination of the patient (such as a CT, MR or ultrasound imaging procedure). The medical product 100 comprises a container 110 (for example, a bottle) that stores the medical liquid 105 (such as with a capacity from 50 to 500 ml). The container 110 is made of an impervious material for containing the medical liquid 105 (for example, glass), which is substantially rigid (i.e., maintaining its shape in normal conditions of use). The container 110 has a main body 115 (for example, of a generic cylindrical shape), which is filled (at least in part) with the medical liquid 105. At one axial extremity thereof, the main body 115 narrows into a neck 120 ending with a (circular) mouth 125, which is used to load the medical liquid 105 into the container 110 and to deliver the medical liquid 105 from it. The mouth 125 is encircled by an (out-turned) rim 130.

As described in detail in the following, the medical product 100 comprises a closure 135 (for example, of plastic material). The closure 135 is fixed to the container 110 for closing its mouth 125 (to prevent losing the medical liquid 105 and to protect it from environment contamination before use); at the same time, the closure 135 allows delivering the medical liquid 105, for example, to a (spike-less) delivery device (not shown in the figure), such as a transfer set of the injection system.

Figure 2:
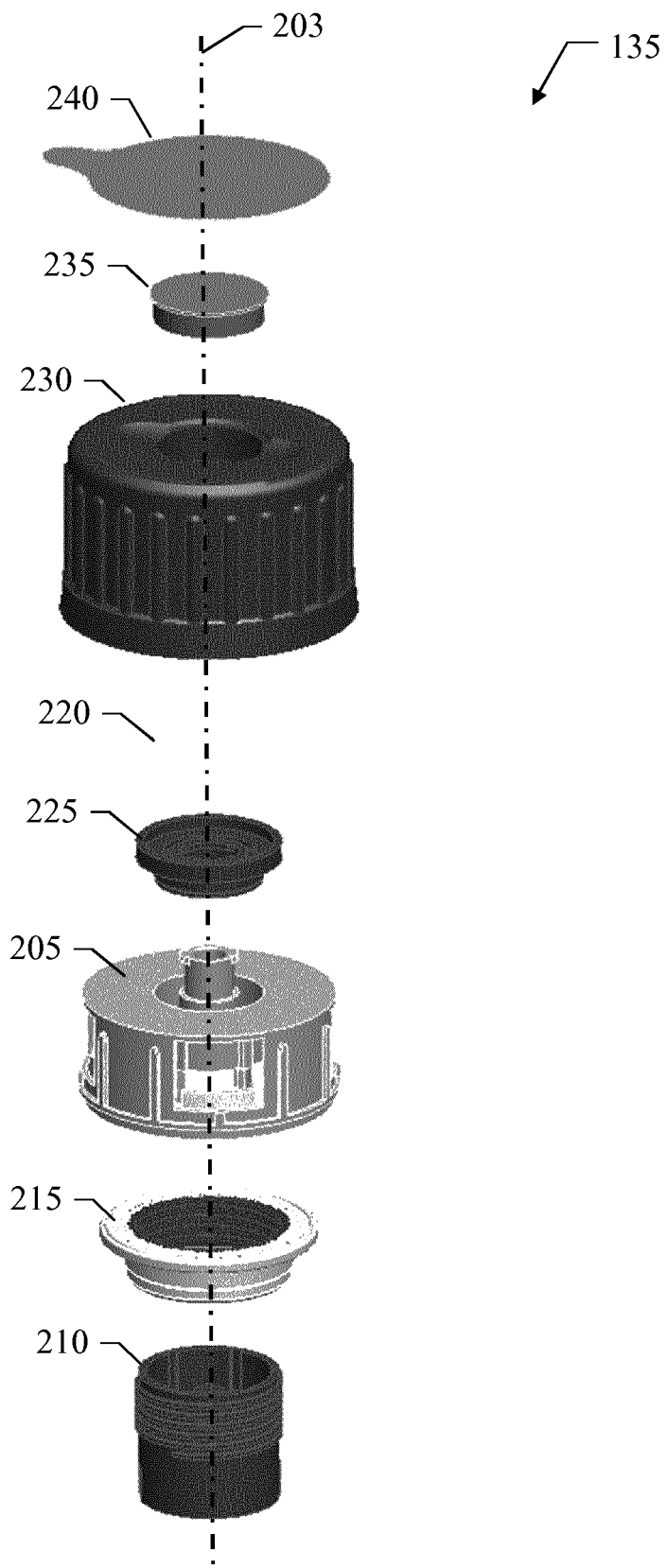
FIG. 2 shows a schematic exploded view of a closure according to an embodiment of the present disclosure.

With reference now to FIG. 2, a schematic exploded view is shown of the closure 135 according to an embodiment of the present disclosure.

The closure 135 comprises the following components (exploded along a longitudinal axis 203 of the closure 135). A cap 205 is used to fix the closure 135 to the container for closing its mouth (not shown in the figure). A cursor 210 is used to act on the cap 205 to control the delivering of the medical liquid and to enable the suctioning of air into the container as the medical liquid is delivered out of the container. An insert 215 is used to screw the cursor 210 and to seal a coupling of the insert 215 with the container (to prevent any leakage of the medical liquid).

In the solution according to an embodiment of the present disclosure, as described in detail in the following, the cap 205 may be rotated around the longitudinal axis 203 of the container 110. The cap 205 is coupled with the cursor 210 so as to drag it in rotation. The cursor 210 is configured to slide with respect to the container as it rotates. As a result, in response to a first rotation of the cap 205 a suction conduit of the cursor 210 breaks a frangible element of the cap 205 (not shown in the figure), so as to enable the suction of air from the external environment into the container (as the medical liquid is delivered out of the container). Moreover, in response to a second rotation of the cap (or to the same first rotation of above) a valve member of the cursor 210 opens a delivery port of the cap 205 (not shown in the figure), so as to enable the delivery of the medical liquid.

The above-described solution is very effective under several points of views.

Particularly, the closure has a spike-less structure that avoids any risk of contaminations and injuries typically correlated to the presence of a spike. Moreover, the suction of the air into the container significantly improves the flow of the medical liquid.

Particularly, this result is achieved by exploiting the valve member (for the medical liquid) and the frangible element (for the air). Therefore, the valve member allows controlling the delivery of the medical liquid with a structure that is very easy to manufacture; at the same time, the frangible element allows maintaining the container closed before use (preventing the suctioning of the air) with a structure that is very simple and of limited dimensions.

The closure of the present disclosure already contains all the components that are necessary for the correct operation thereof. This means that the medical product provided with it is ready to be used, as well as very safe and easy for an operator to manage and work (for example, there is no need of any additional needle for accessing the inside of the container).

In view of the above, the use of the medical product provided with this closure is very easy. Particularly, the breaking of the frangible element and the opening of the delivery port is obtained by acting externally on the closure by hand, simply rotating it.

Moreover, a filter 220 is used to filter the air that is suctioned into the container. A holder 225 is used to hold the filter 220. A cover 230 is used to cover the above-mentioned components 205-225 of the closure 135 (to prevent access to the fixing of the cap 205 to the container, to protect the components 205-225 from the external environment and to provide a good grip to the operator acting on the closure 135 at the same time preventing breakage of gloves usually worn by him/her). A lid 235 is used to close an opening of the cover 230 (to protect the components exposed through it before use). A protection film 240 is used to complete a sealing of the cover 230 (to prevent contamination and to ensure integrity of the medical product 100 before use).

Figure 3:
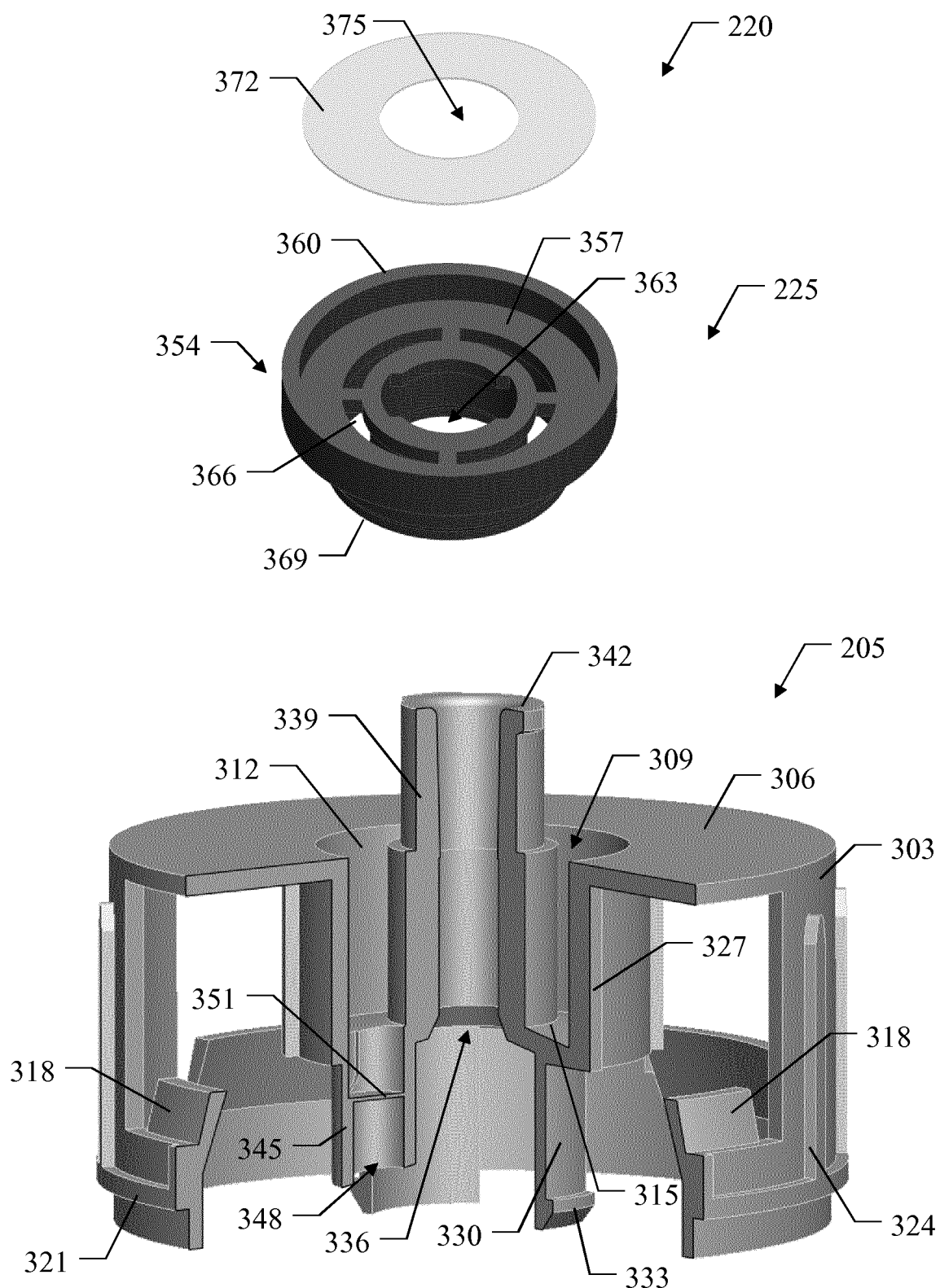
FIG. 3-FIG. 5 show schematic exploded views of some components of the closure according to an embodiment of the present disclosure.
Figure 4:
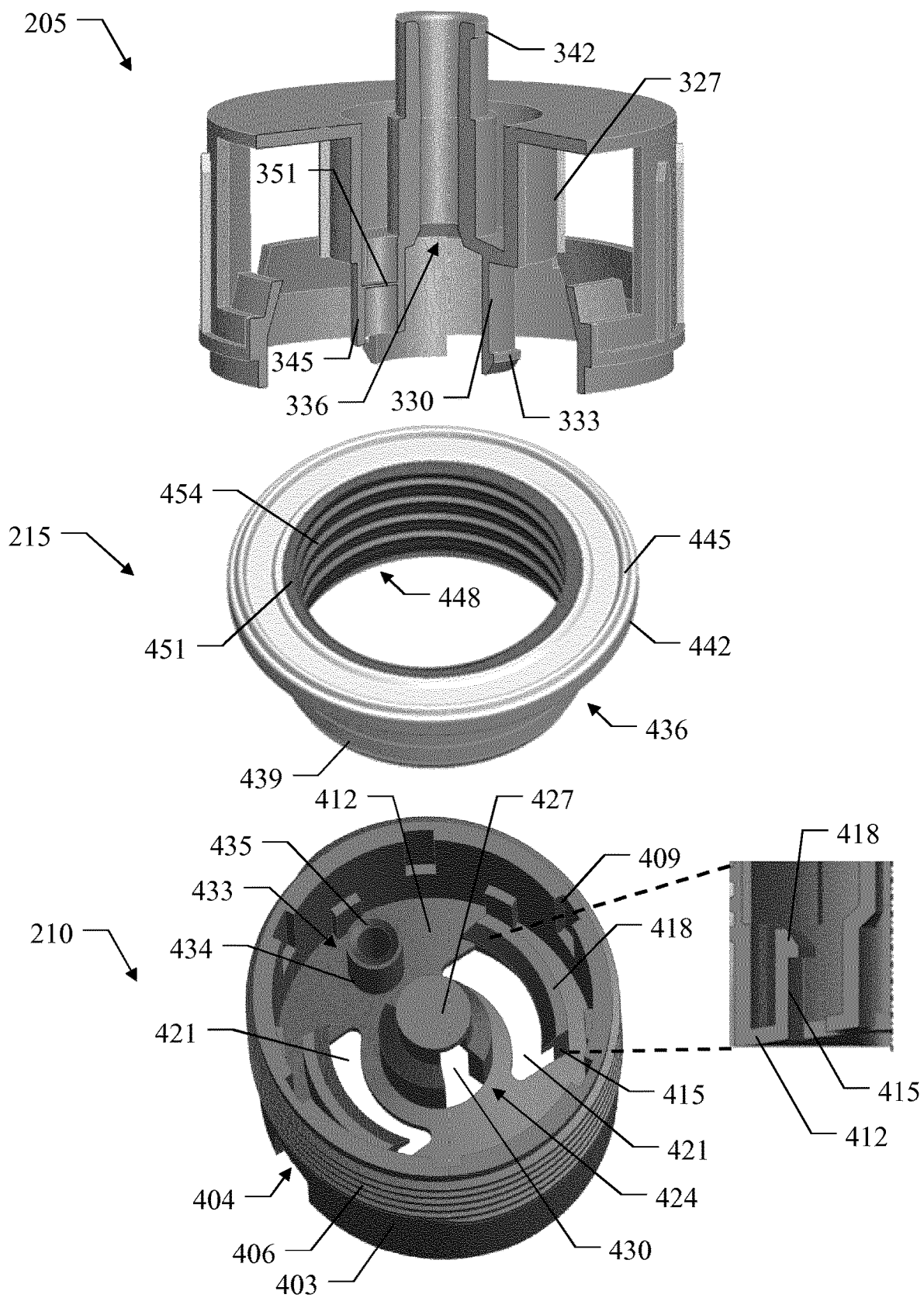
Figure 5:
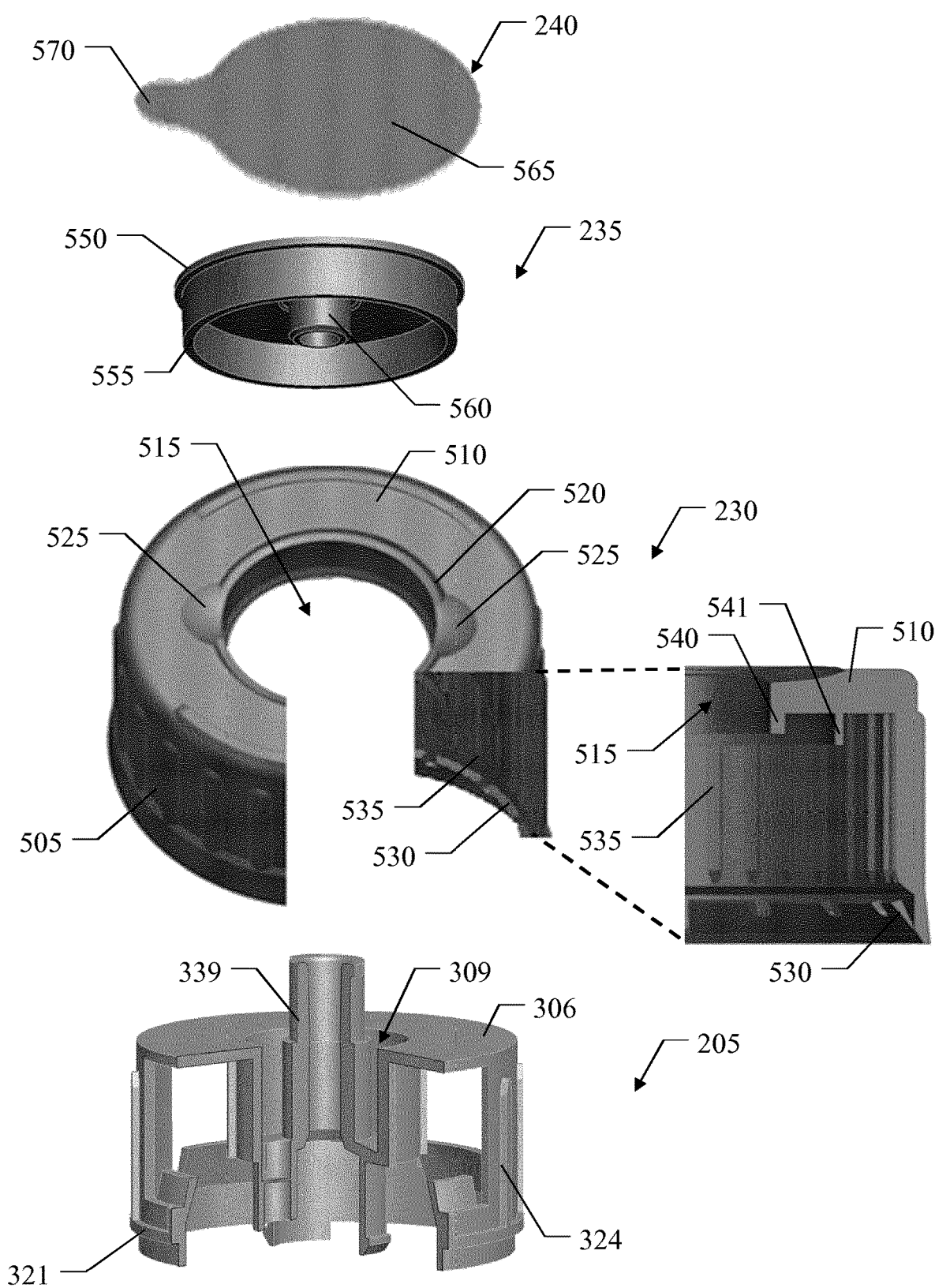

With reference now to FIG. 3-FIG. 5, schematic exploded views are shown of some components of the closure according to an embodiment of the present disclosure.

Starting from FIG. 3, the cap 205 (shown in partially cut-away view) is a body (for example, made from polypropylene homopolymer, PPH, by injection molding) with a generic hollow cylindrical shape (matching the neck of the container, not shown in the figure), which is defined by a lateral wall 303 closed at the top (facing outwards the container in a fixed condition, wherein the closure is fixed to the container) by a disk 306 (whereas it is open at the opposite end thereof, i.e., at the bottom). The disk 306 has a central depression 309 for housing a part of the holder 225 (with a depth lower than a height of the lateral wall 303); the depression 309 is delimited by a lateral wall 312 and a bottom wall 315. One or more teeth 318 (for example, from 4 to 8) project inwards from the lateral wall 303, slightly inside a free border thereof, for fixing to the container; the teeth 318 extend obliquely, towards the inside of the cap 205 (i.e., towards the disk 306). A rim 321 projects outwards from the lateral wall 303 close to its free border for fixing the cover (not shown in the figure). A plurality of ribs 324 (for example, from 5 to 10) project outwards from the lateral wall 303, longitudinally along it, for interfering rotationally with the cover. A plurality of (further) ribs 327 (for example, from 4 to 8) project outwards from the lateral wall 312, longitudinally along it, for interfering rotationally with the cursor (not shown in the figure). One or more tabs 330 (for example, from 2 to 4) projects downwards (inwards in the fixed condition) from the bottom wall 315 (slightly inside a border thereof) for stopping the cursor axially; the tabs 330 end with corresponding teeth 333 projecting radially outwards, for engaging with corresponding teeth of the cursor.

A delivery port 336 is open at the center of the bottom wall 315 for delivering the medical liquid from the container; the delivery port 336 has a size corresponding to a desired flow rate of the medical liquid (for example, it has a cross-section from 10 to 40 mm$^2$). A delivery conduit 339 extends upwards (outwards in the fixed condition) from the delivery port 336; the delivery conduit 339 is higher than the depth of the depression 309, so that a portion of the delivery conduit 339 projects above (outside in the fixed condition) the disk 306. An axial free end of the delivery conduit 339 (projecting above the disk 306) is configured as a connector 342 for matching with the delivery device (not shown in the figure), to be connected thereto for delivering the medical fluid from the container. For example, the connector 342 is a female luer lock fitting comprising a tabbed hub with an external thread for engaging with a male luer lock fitting of the delivery device.

A first suction conduit, referred to as cap suction conduit 345, extends downwards (inwards in the fixed condition) from the periphery of the bottom wall 315 (for example, without reaching the free border of the lateral wall 303) for suctioning air from the external environment into the container during the delivery of the medical liquid. As a result, an axial free end 348 of the cap suction conduit 345 (distal from the bottom wall 315) is spaced apart longitudinally from the delivery port 336 by the length of the cap suction conduit 345 (for example, by 4-12 mm, preferably by 5-10 mm and still more preferably by 6-8 mm, such as by 7 mm), so that in the fixed condition this free end 348 is positioned more in depth within the container (and thus more far away from the mouth of the container) than the delivery port 336. The size of the cap suction conduit 345 is designed in order to obtain the desired flow rate of the medical liquid to be delivered through the delivery port 336.

A frangible element 351 (i.e., an element which may be broken relatively easily, instead of deforming) closes the cap suction conduit 345. For example, the frangible element 351 is a membrane that is attached through its border to an internal wall of the cap suction conduit 345 at a predetermined height thereof (for example, at the middle). Preferably, the membrane has pre-cut lines, extending along a substantial portion of the circumference thereof, which facilitate its breaking without losing parts inside the container (and thus in the medical liquid) and without detaching from the internal wall of the cap suction conduit 345.

The holder 225 is a body (for example, made from polypropylene, PP, or acrylonitrile butadiene styrene, ABS) with a generic cylindrical shape. The holder 225 comprises a hollow tray 354 for holding the filter 220. The hollow tray 354 is formed by a (flat) ring 357 with an (external) raised edge 360; the ring 357 has an external diameter larger than an internal diameter of the depression 309 and the raised edge 360 has a height larger than a thickness of the filter 220. The ring 357 has a (central) through-hole 363. One or more windows 366 (for example, from 2 to 8) are provided in the ring 357, around the through-hole 363, for exposing the filter 220. The windows 366 are larger than a cross-section of the cap suction conduit 345. A hollow turret 369 (for example, formed by two concentric cylindrical walls) extends downwards (inwards in the fixed condition) from the ring 357 around its through-hole 363. The hollow turret 369 has an internal diameter matching an external diameter of the delivery conduit 339 of the cap 205 and an external diameter matching an internal diameter of the depression 309 of the cap 205.

The filter 220 comprises an anti-bacterial membrane shaped as a ring 372 with a central through-hole 375. The ring 372 of the filter 220 matches the ring 357 of the holder 225 (i.e., the ring 372 has an external diameter matching an internal diameter of the raised edge 360 and the through-hole 375 of the filter 220 matches the through-hole 363 of the holder 225).

Moving to FIG. 4, the cursor 210 is a body (for example, made from cyclic olefin copolymer, COC, cyclic olefin copolymer, COP, or propylene carbonate, PC, by injection molding) with a generic hollow cylindrical shape. Particularly, the cursor 210 comprises a lateral wall 403 with one or more saddles 404 (for example, from 2 to 4) extending from an axial end thereof facing inwards the container, not shown in the figure (inwards in the fixed condition), for the passage of the medical liquid. The lateral wall 403 has an (external) thread 406 for screwing into the insert 215; the thread 406 extends longitudinally around a portion of the cursor 210, from another axial end thereof facing upwards (outwards in the fixed condition) to a middle thereof. A plurality of grooves 409 are formed inside the lateral wall 403, longitudinally along it, for engaging with the ribs 327 of the cap 205. A partition wall 412 extends transversally inside the lateral wall 403, at the middle thereof. As better visible in a corresponding enlarged portion of the cursor 210, one or more tabs 415, corresponding to the tabs 330 of the cap 205, projects upwards (outwards in the fixed condition) from the partition wall 412; the tabs 415 end with corresponding teeth 418 projecting radially inwards, for engaging with the teeth 333 of the cap 205. One or more windows 421 are provided in the partition wall 412 (slightly inside the tabs 415), for example, in front of the saddles 404, for the passage of the medical liquid and of the tabs 330 of the cap 205.

The cursor 210 comprises a valve member 424 for opening/closing the delivery port 336 of the cap 205. The valve member 424 is formed of a turret 427 that extends upwards (outwards in the fixed condition) from a center of the partition wall 412. The turret 427 is hollow inside, i.e., from below the partition wall 412 (internally in the fixed condition); one or more lateral windows 430 (for example, from 2 to 4) are provided in the turret 427 for the passage of the medical liquid. A second suction conduit, referred to as cursor suction conduit 433, extends upwards (outwards in the fixed condition) from the partition wall 412 (i.e., the cursor suction conduit 433 originates from the region comprised between the valve member 424 and the lateral wall 403). An external diameter of the cursor suction conduit 433 matches in width an internal diameter of the cap suction conduit 345 for sliding therein (while the cursor suction conduit 433 is slightly shorter than the cap suction conduit 345). A corresponding opening formed by the cursor suction conduit 433 at the partition wall 412 defines a suction port 434 for suctioning air from the external environment into the container during the delivery of the medical liquid. An axial free (upper) end of the cursor suction conduit 433 (distal from the partition wall 412) is slanted so as to define a sharpened tip 435 for acting on the frangible element 351.

Generally, the delivery port 336 and the suction port 434 differ structurally (in addition to for their use). Particularly, the suction port 434 is smaller in cross-section area than the delivery port 336 (for example, the cross-section area of the suction port 434 is about 25-75% of the cross-section area of the delivery port 336). The delivery port 336 is in fluid communication with the connector 342, whereas no connector is generally required for the suction port 434. Moreover, the suction port 434 is coupled with the filter (not shown in the figure), whereas no filter is generally required for the delivery port 336.

The insert 215 is a body with a generic hollow cylindrical shape, which is preferably made from two different materials by overmolding.

Particularly, the insert 215 comprises an external portion 436 operating as a gasket. The external portion 436 is made of an elastic material (for example, polypropylene homopolymer, PPH). The external portion 436 comprises a (hollow) elastic cylinder 439; an external diameter of the elastic cylinder 439 is slightly higher than an internal diameter of the mouth of the container (not shown in the figure) for press-fitting therein. An elastic flange 442 extends outwards from an axial upper end (outer in the fixed condition) of the elastic cylinder 439; the elastic flange 442 defines an O-ring having a width matching an edge of the mouth of the container for sealing it. One or more bulging rings 445 project upwards (outwards in the fixed condition) slightly inside an external border of the elastic flange 442; the bulging rings 445 are significantly thinner than the elastic flange 442 (for example, a width of each bulging ring 445 is equal to 1-20%, preferably 2-15% and still more preferably 3-10%, such as 5% of a width of the elastic flange 442) for reducing a contact surface with the cap 205.

Moreover, the insert 215 comprises an internal portion 448 operating as a bush. The internal portion 448 is made of a more rigid material (for example, styrene ethylene butylene styrene copolymer, SEBS). The internal portion 448 comprises a hollow cylinder 451; an internal diameter of the hollow cylinder 451 matches an external diameter of the cursor 210. The hollow cylinder 448 is provided with an (internal) thread 454 matching the external thread 406 of the cursor 210 for its screwing; the thread 454 extends longitudinally along the whole length of hollow cylinder 448.

Moving to FIG. 5, the cover 230 (shown in partially cut-away view) is a body (for example, made from polypropylene, PP) with a generic hollow cylindrical shape (matching the cap 205), which is defined by a lateral wall 505 that is closed at the top (externally in the fixed condition) by a disk 510 (whereas it is open at the opposite end thereof, i.e., at the bottom). The disk 510 has a central through-hole 515; the through-hole 515 has a diameter matching a diameter of the depression 309 of the cap 205. A counterbore 520 is formed around the through-hole 515 matching the lid 235. One or more access dips 525 are provided outside the disk 510 starting from the counterbore 520 for pulling the lid 235. A ring with one or more teeth 530 (for example, from 4 to 8) project inwards from the lateral wall 505, slightly inside a free border thereof, for interfering with the rim 321 of the cap 205; the teeth 530 extend obliquely, towards the inside of the cover 230. A plurality of ribs 535 project inwards from the lateral wall 505, longitudinally along it, for engaging with the ribs 324 of the cap 205 (for example, with one rib 324 of the cap 205 every 2-4 ribs 535 of the cover 230). As better visible in a corresponding enlarged portion of the cover 230, a crown 540 extends downwards (inwards in operation) from a border of the through-hole 515 and another crown 541 extends downwards from the disk 510 around the crown 540; the crown 541 has a height corresponding to the portion of the delivery conduit 339 projecting outside the disk 306 of the cap 205, whereas the crown 540 has a height slightly shorter than it.

The lid 235 (for example, made from polypropylene, PP, or a thermoplastic elastomer) comprises a disk 550, which matches in width and in height the counterbore 520. A crown 555 extends downwards (inwards in the fixed condition), starting slightly inside a border of the disk 550. The crown 555 is remarkably shorter than the crown 540; the crown 555 has an external diameter matching an internal diameter of the crown 540. A (hollow) turret 560 extends downwards (inwards in the fixed condition) from a center of the disk 550; the turret 560 has a height equal to (or slightly lower than) a height of the crown 555 and an external diameter matching an internal diameter of the delivery conduit 339 of the cap 205.

The protection film 240 (for example, made from aluminum) comprises a circular body 565 (slightly larger than the through-hole 515), with a handling tab 570 projecting laterally from it.

With reference now to FIG. 6A-FIG. 6E, the main steps are shown of a process for assembling the closure according to an embodiment of the present disclosure.

Figure 6A:
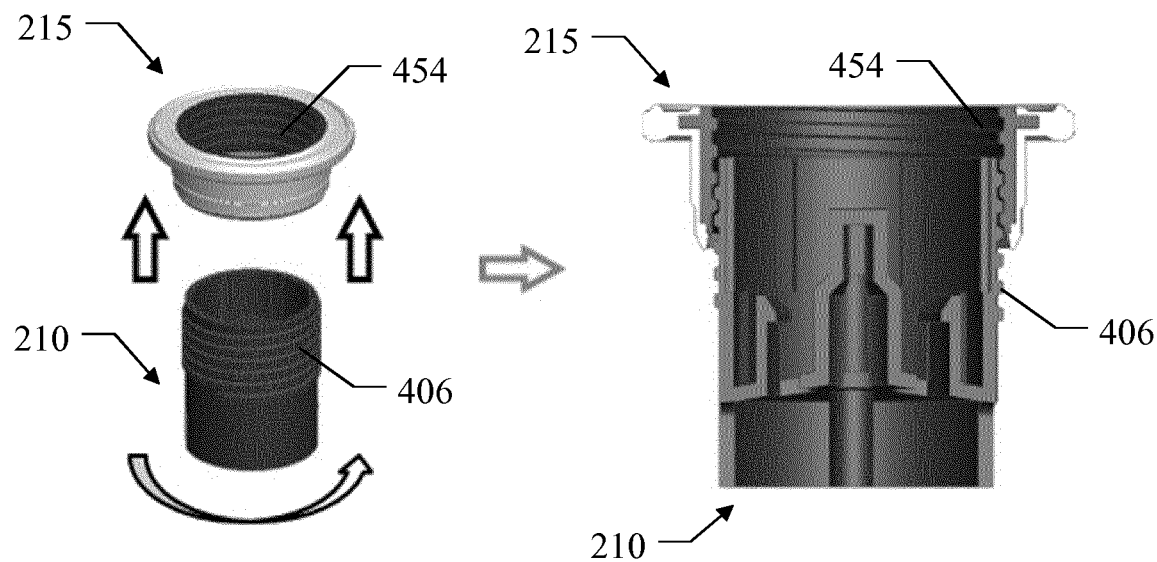
FIG. 6A-FIG. 6E show the main steps of a process for assembling the closure according to an embodiment of the present disclosure.

Starting from FIG. 6A, the cursor 210 is mounted inside the insert 215 (from below, as indicated by the arrows) by screwing the thread 406 of the cursor 210 onto the thread 454 of the insert 215 (for example, clockwise as indicated by the arrow). The cursor 210 is screwed to an extent ensuring its proper operation (as described in the following) but without the cursor 210 exiting from the insert 215 at the opposite side (above in the figure).

Figure 6B:
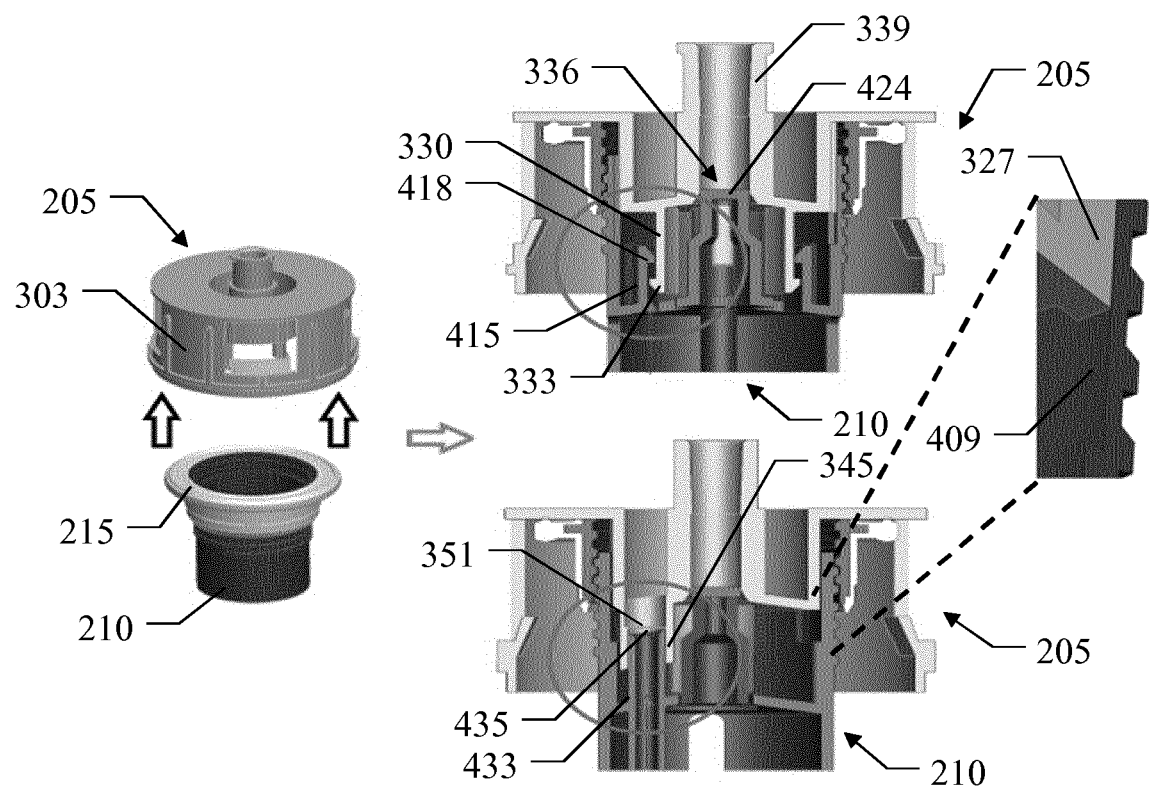

Moving to FIG. 6B, the assembly 210-215 so obtained is snap fitted into the cap 205 by pushing it (from below, as indicated by the arrows) within the lateral wall 303, with the insert 215 forward-facing (upwards). The assembly 210-215 and the cap 205 are pre-oriented so that the cursor suction conduit 433 is aligned with the cap suction conduit 345; as a consequence, as better visible in a corresponding enlarged portion of the cap 205 and the cursor 210, the grooves 409 of the cursor 210 are aligned with the corresponding ribs 327 of the cap 205; at the same time, the tabs 415 of the cursor 210 are aligned with the tabs 330 of the cap 205.

As shown in the two cross-section views along different planes, when during this operation the teeth 418 of the cursor 210 reach the teeth 333 of the cap 205, the interference of their front lead-in faces causes the corresponding tabs 415 and tabs 330 to yield elastically (spacing apart), thereby allowing their passage (with the teeth 418 and the teeth 333 that then return elastically to their original position as soon as they clear). At the same time, the valve member 424 of the cursor 210 enters into the delivery conduit 339 of the cap 205 (through its delivery port 336). As a result, the valve member 424 is brought to a closed position. Particularly, the valve member 424 is press-fitted into the delivery conduit 339 (thanks to their interference), so as to seal it. Moreover, the cursor suction conduit 433 enters the cap suction conduit 345, but to an extent that the sharpened tip 435 of the cursor suction conduit 433 does not reach (and thus does not break) the frangible element 351.

Figure 6C:
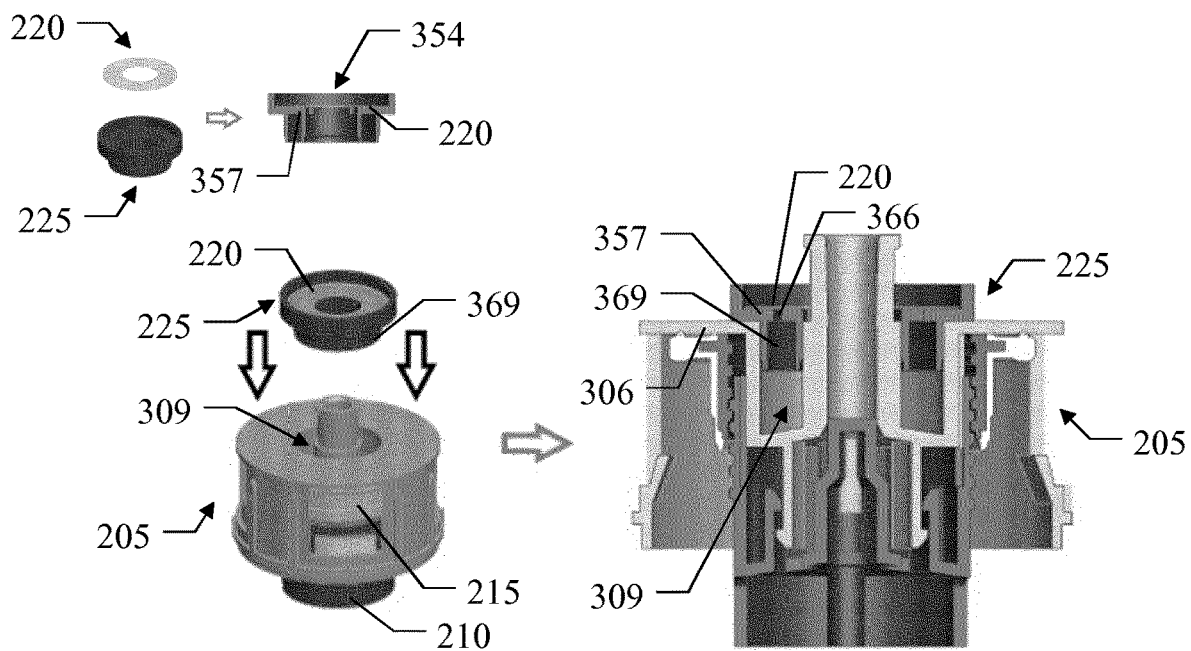

Moving to FIG. 6C, before, concurrently or after the above-mentioned operations, the filter 220 is fixed into the holder 225 by pushing it (from above) into the tray 354, until the filter 220 abuts against the ring 357, wherein it is heat-sealed or glued. In this way, a corresponding portion of the filter 220 is exposed through the windows 366 of the holder 225.

The holder 225 (with the filter 220) is mounted into the cap 205 (already provided with the cursor 210 and the insert 215) by pushing it (from above, as indicated by the arrows) into the depression 309, with its hollow turret 369 forward-facing (downwards). The holder 225 is pushed until the ring 357 abuts against the disk 306 of the cap 205. As a result, the hollow turret 369 of the holder 225 is press-fitted into the depression 309.

Figure 6D:
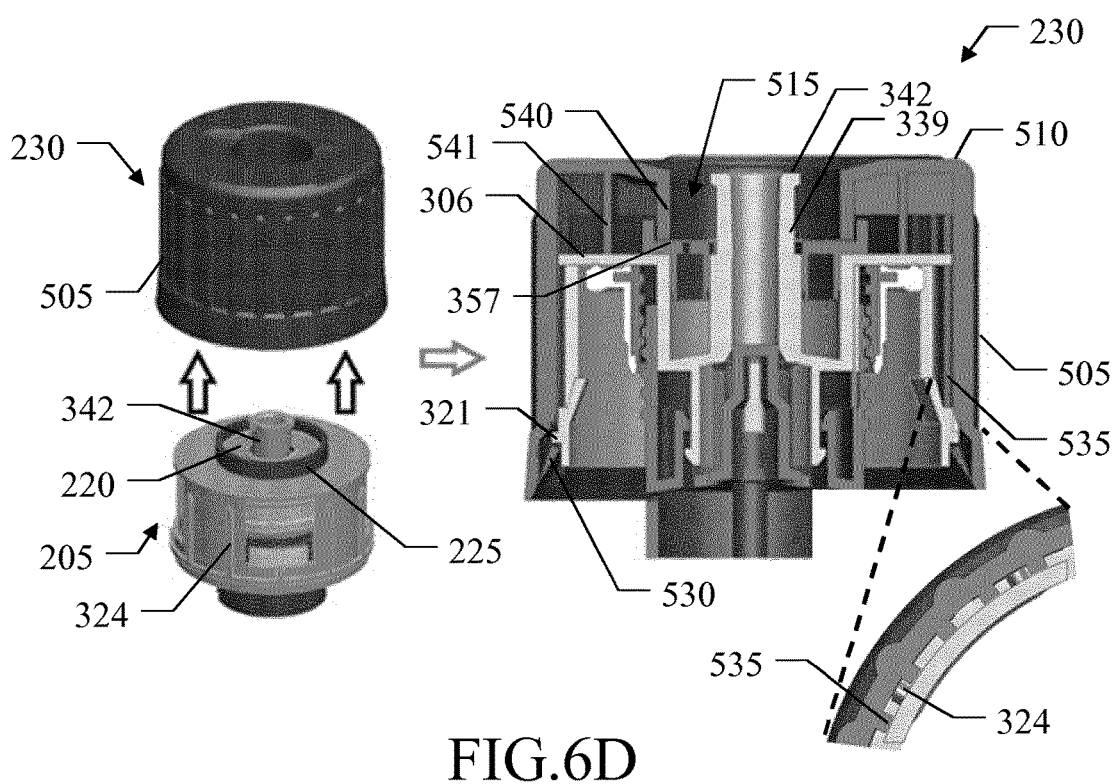

Moving to FIG. 6D, the cap 205 (already provided with the above-mentioned components) is snap fitted into the cover 230 by pushing it (from below, as indicated by the arrows) within the lateral wall 505, with the connector 342 forward-facing (upwards). As better visible in a corresponding enlarged portion of the cap 205 and the cover 230, they are pre-oriented so that the corresponding ribs 324 and 535 are staggered. When during this operation the teeth 530 of the cover 230 are reached by the rim 321 of the cap 205, the orientation of the teeth 530 towards the inside of the cover 230 causes their resilient yielding, thereby allowing the passage of the rim 321 and the final engagement of the cover 230 onto the cap 205 (with the teeth 530 that then return elastically to their original position). The cap 205 is pushed until the ring 357 of the holder 225 and the disk 306 of the cap 205 abut against the crown 540 and the crown 541, respectively, of the cover 230, thereby having the delivery conduit 339 projecting into the through-hole 515 (slightly below the level of the disk 510). As a result, the cover 230 securely retains the holder 225 (and then the filter 220) in place. Moreover, the interlocking of the teeth 530 with the rim 321 fixes together the cover 230 and the cap 205; since the teeth 530 are not accessible from the outside of the cover 230 when the closure is mounted on the container (not shown in the figure), the fixing is non-reversible (i.e., it is not possible, or at least it is very difficult, to remove the cover 230 from the cap 205 without breaking it). At the same time, the ribs 324 and 535 slot in, so as to prevent any relative rotation of the cover 230 and the cap 205.

Figure 6E:
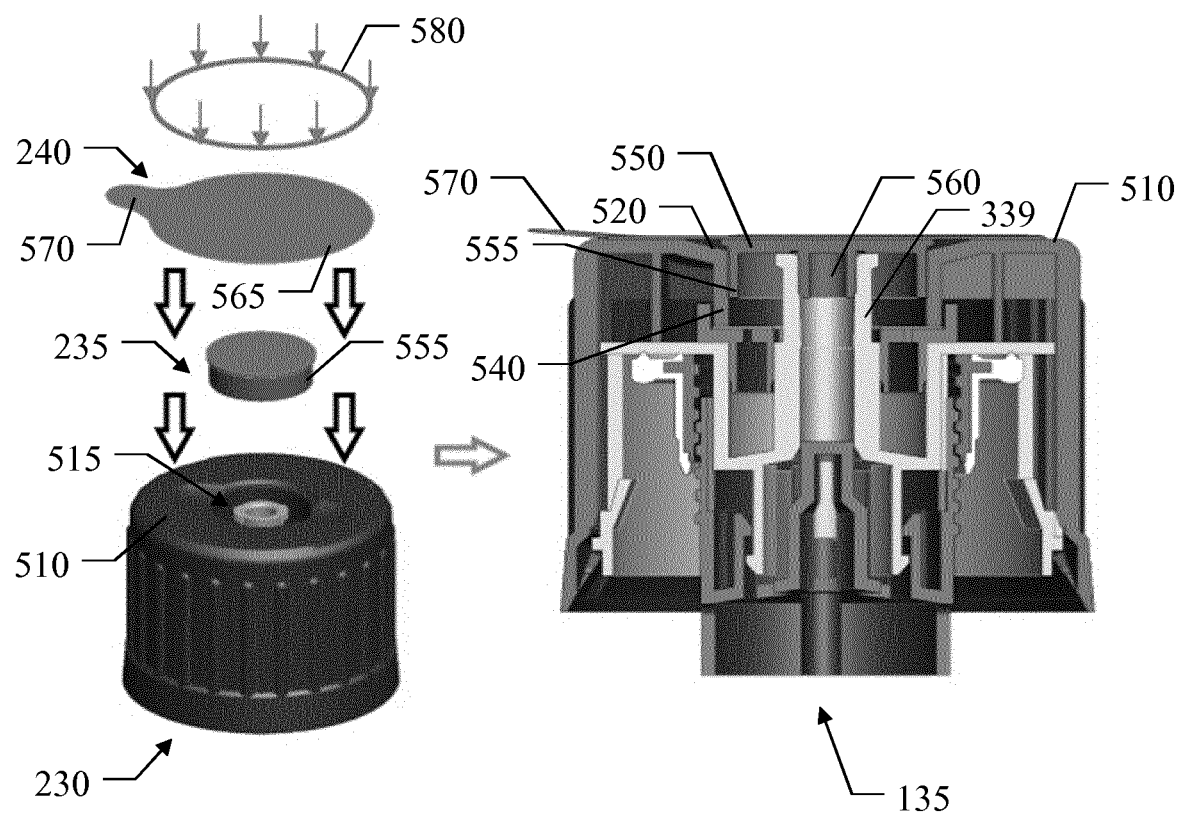

Moving to FIG. 6E, the lid 235 is mounted into the cover 230 (already provided with all the above-mentioned components) by pushing it (from above, as indicated by the arrows) into the through-hole 515, with its crown 555 forward-facing (downwards). The lid 235 is pushed until the disk 550 abuts against the counterbore 520 of the cover 230. As a result, the crown 555 and the turret 560 of the lid 235 are press-fitted into the crown 540 and into the delivery conduit 339, respectively (with their interference that retains the lid 235 in place). At this point, the protection film 240 is placed over the cover 230, with its circular body 565 positioned around the through-hole 515 (thereby covering the lid 235) and its handling tab 570 slightly and freely projecting outside the disk 510 of the cover 230. The protection film 240 is welded (i.e., heat sealed) or glued to the disk 510 along a border of the circular body 565, so as to complete the closure 135. Reference 580 shows an example of distribution of welded joints at the peripheral border of the protection film 240 in order to associate the latter with the disk 510. In this way, the protection film 240 is attached to the cover 230 in a peelable way (i.e., so as to be easily detachable by the user's hands without requiring any tool).

In view of the above, the closure may be assembled automatically and then at low cost. Moreover, all the components of the closure of the present disclosure may be easily associated by means of a pushing force, fact which advantageously simplifies its manufacturing.

Figure 7:
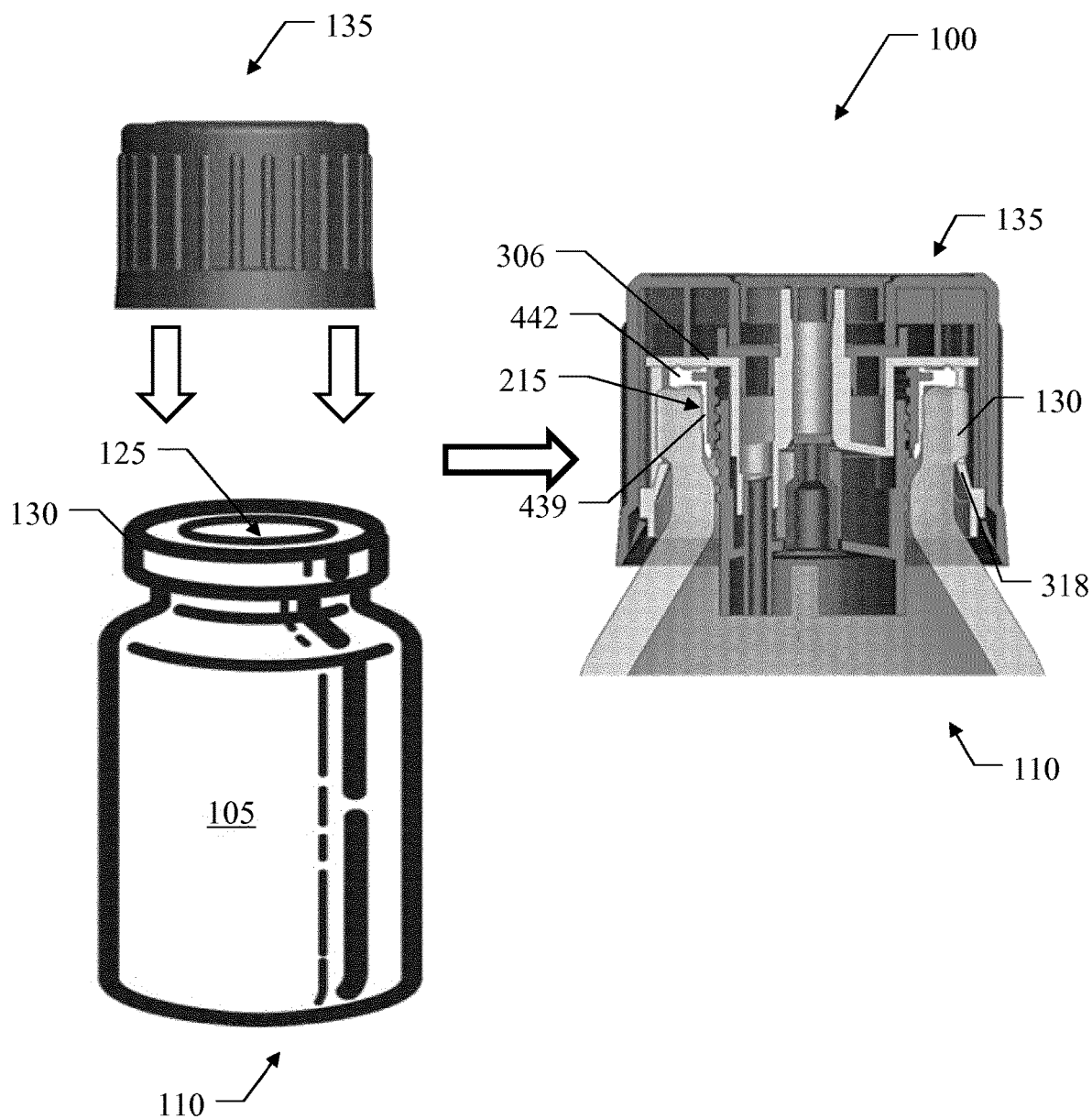
FIG. 7 shows the main steps of a process for manufacturing the medical product according to an embodiment of the present disclosure.

With reference now to FIG. 7, the main steps are shown of a process for manufacturing the medical product 100 according to an embodiment of the present disclosure.

The container 110 is filled through its mouth 125 with the medical liquid 105. At this point, the closure 135 (possibly after a preliminary sterilization thereof) is snap fitted onto the container 110 by pushing it (from above, as indicated by the arrows) onto the mouth 125, with its open end forward-facing (downwards). When the teeth 318 of the closure 135 engage the rim 130 of the container 110, the inwards orientation of the teeth 318 causes their resilient yielding, thereby allowing the closure 135 to pass over the rim 130 and to fix to the container 110 (with the teeth 318 that then return elastically to their original position as soon as the rim 130 has been overcome, thereby guaranteeing the necessary grip force). At the same time, the elastic cylinder 439 of the insert 215 is press-fitted into the mouth 125 (thanks to their interference). The closure 135 is pushed until the disk 306 abuts against an edge of the mouth 125, through the elastic flange 442 of the insert 215 compressed between them. As a result, when the pushing force onto the closure 135 is released, the elastic flange 442 elastically tends to return to its original shape. In this way, the elastic flange 442 pushes the closure 135 away from the container 110 (upwards) and, as a result thereof, the teeth 318 are forced against an undercut of the rim 130, and thus the closure 135 in firmly fixed to the container 110. Moreover, since the teeth 318 are not accessible from the outside of the closure 135, the fixing is non-reversible (i.e., it is not possible, or at least it is very difficult, to remove the closure 135 from the container 110 without breaking it). This prevents (or at least substantially hinders) any tampering of the medical product 100. Indeed, the closure 135 may be detached from the container 110 only by breaking the closure 135 itself and thus rendering the latter unsuitable for a successive use. This aspect clearly improves the safety of the medical product 100. At the same time, the (at least partially compressed) elastic cylinder 439 and elastic flange 442 of the insert 215 seal the container 110 from the external environment.

The medical product 100 is then sterilized in an autoclave (not shown in the figure). The closure 135 is configured (for example, according to the rigidity of the teeth 318) so as to ensure its fixing to the container 110 during this sterilization phase, especially during a warming transient thereof (wherein a relatively high pressure is created inside the container 110, not compensated yet by pressurized air injected into the autoclave).

In view of the above, the medical product may be assembled automatically and then at low cost. Moreover, the closure of the present disclosure may be easily associated with the container by means of a pushing force, fact which advantageously simplifies the manufacturing of the final medical product. The closure of the present disclosure, thanks to its insert, may also be mounted onto any standard container made from any material, without requiring any specific modification of the container itself (for example, of its neck provided that it is sufficiently rigid for allowing a correct coupling with the closure).

With reference now to FIG. 8A-FIG. 8G, the main steps are shown of a process for using the medical product according to an embodiment of the present disclosure.

Figure 8A:
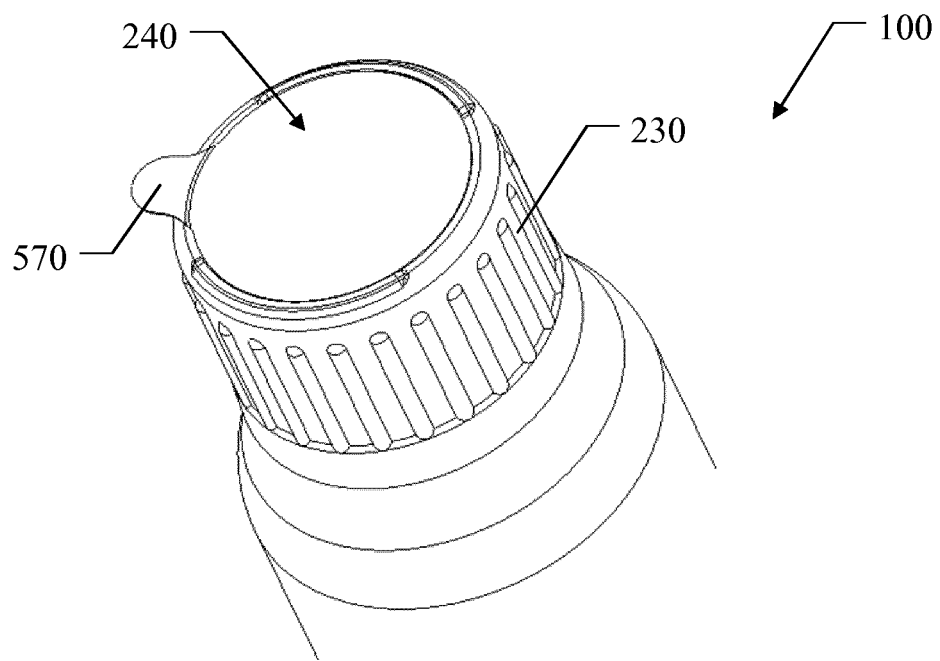
FIG. 8A-FIG. 8G show the main steps of a process for using the medical product according to an embodiment of the present disclosure.

Starting from FIG. 8A, when the medical product 100 has to be used (for example, to perform an injection as part of a CT scan examination of a patient), the operator, such as a healthcare assistant, at first removes the protection film 240. For this purpose, the operator grasps the handling tab 570 freely projecting outside the cover 230; the operator then pulls the handling tab 570 away from the cover 230 (in opposition to its welding thereto) so as to peel off the protection film 240.

Figure 8B:
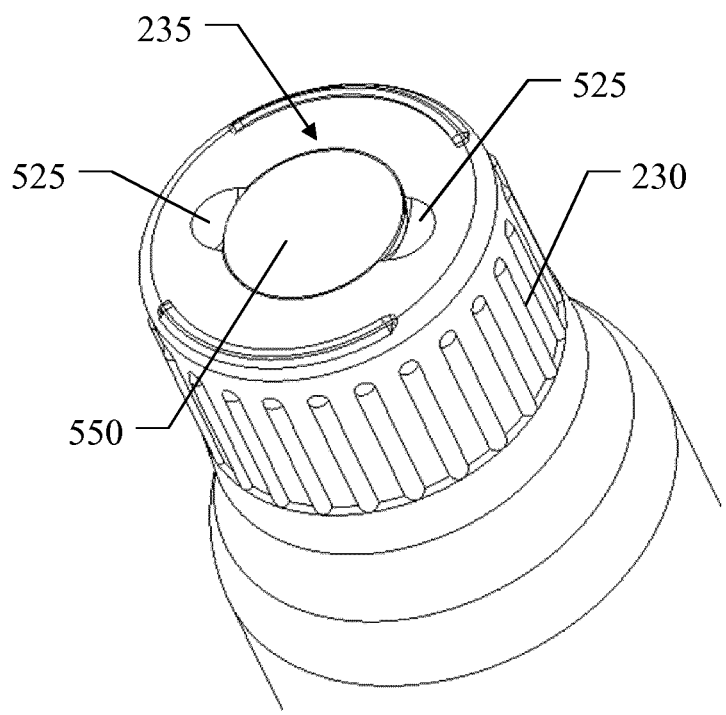

Moving to FIG. 8B, the operator removes the lid 235. For this purpose, the operator pinches the disk 550 by inserting the tips of two fingers into the access dips 525; the operator then pulls the disk 550 away from the cover 230 (in opposition to its press-fitting therein) so as to detach the lid 235 from the cover 230.

Figure 8C:
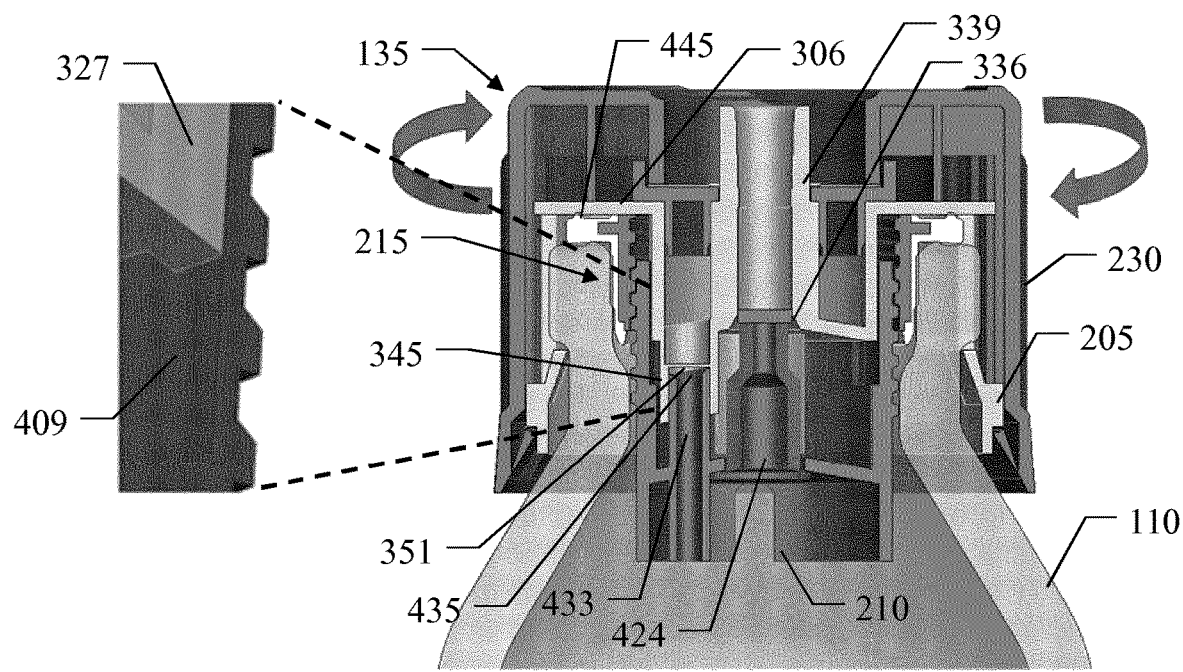

Moving to FIG. 8C, the operator rotates the closure 135 by acting onto the cover 230 (for example, clockwise as indicated by the arrows). The cover 230 drags the cap 205 thereby transferring its rotation thereto, thanks to the mechanical coupling of their staggered ribs (not visible in the figure); in turn, the cap 205 drags the cursor 210 thereby transferring its rotation thereto, thanks to the interference of the ribs 327 of the cap 205 with the grooves 409 of the cursor 210 (as better visible in a corresponding enlarged portion thereof). The insert 215 instead remains integral with the container 110, thanks to their friction; moreover, the bulging rings 445 reduce a contact surface between the insert 215 and the disk 306 of the cap 205, and then a corresponding friction, so as to prevent (or at least substantially limit) the cap 205 from dragging the insert 215 during the rotation thereof. As a result, the cursor 210 screws into the insert 215, so as to translate upwards (outwards the container 110).

The cursor suction conduit 433 then slides accordingly (upwards) along the cap suction conduit 345. As soon as the sharpened tip 435 of the cursor suction conduit 433 reaches the frangible element 351, the sharpened tip 435 breaks the frangible element 351 (see FIG. 8D); the configuration of the sharpened tip 435 facilitates the breaking of the frangible element 351, without any risk of detachment of particles thereof. The (broken) frangible element 351 remains attached to the border of the cap suction conduit 345, housed into a corresponding notch formed therein (not shown in the figure), so as to remain adherent to the cap suction conduit 345 thereby avoiding any risk of blocking the passage of the air.

Figure 8D:
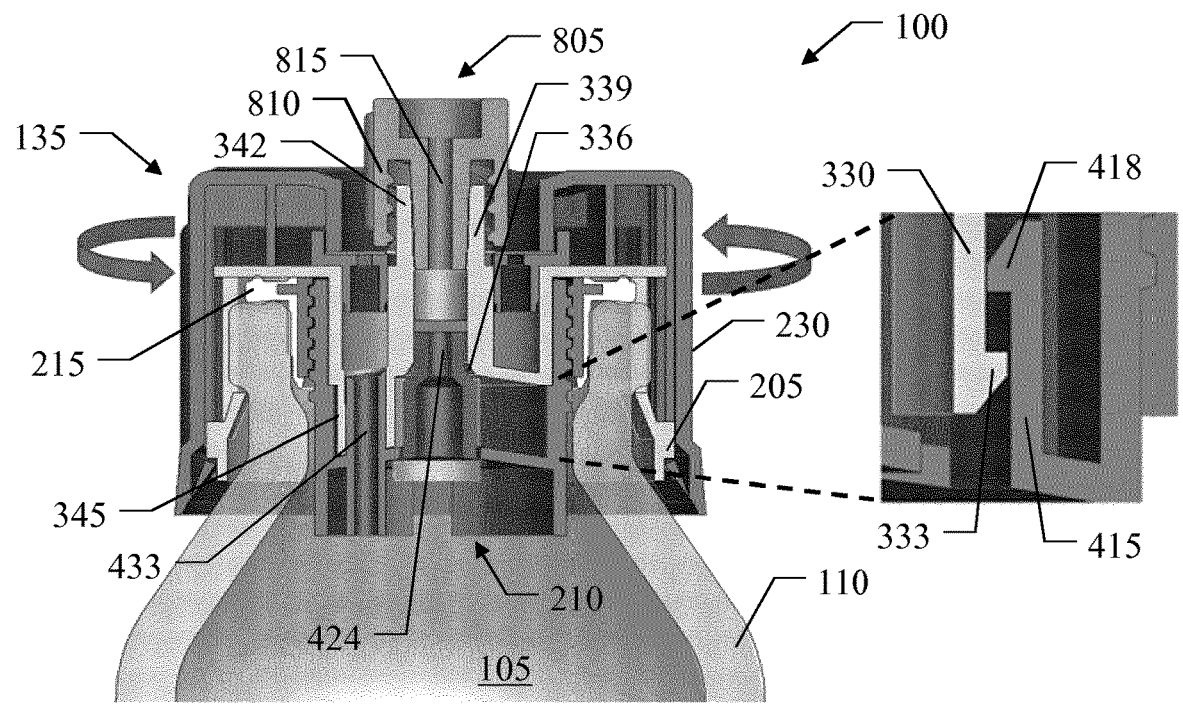

At the same time, the valve member 424 as well slides accordingly (upwards) along the delivery conduit 339 further entering therein, and then maintaining the delivery port 336 closed (see FIG. 8D). The closure 135 is rotated until bottom walls of the grooves 409 of the cursor 210 abut against axial free ends of the ribs 327 of the cap 205. Since the cursor 210 is already partially screwed into the insert 215 (during the assembling of the closure 135), this (breakage) end-of-stroke position is reached with a relatively short rotation (for example, from 1.5 to 2.0 turns, such as 1.8 turns). Therefore, the operation of breaking the frangible element 351 is very fast.

As shown in FIG. 8D, the operator connects the medical product 100 to the delivery device (not shown in the figure).

For example, the delivery device may be a syringe to be filled with the medical liquid 105 present in the container 110. Typically, the syringe is a needle-less syringe having a tip provided with a connector that suitably matches and engages the connector 342 of the closure 135. Preferably, the syringe (once it has been filled with the medical liquid 105) becomes a pre-filled syringe that is used in syringe injectors (for example, Empower CTA or Empower CTA+ manufactured by Bracco Injeneering SA, trademarks) for injecting a contrast agent, a saline solution, a therapeutic substance (for example, a drug) and/or a combination thereof during a diagnostic procedure (for example, a CT, MR or ultrasound imaging applications) or a therapeutic infusion. Alternatively, the delivery device may be a syringe-less injector (for example, CT Exprès manufactured by Bracco Injeneering SA, trademarks). In particular, the connector 342 may be engaged by a connector provided at a free end of a transfer line, which connects a supply station to a pressurizing unit (for example, a peristaltic pump) of the injector. The supply station (typically from two to three for each injector) comprises a container (a bottle or a bag) for supplying the medical liquid (for example, contrast agent, saline or a combination thereof) to be injected into a patient during a scan examination (for example, a CT imaging procedure). A transfer line is typically provided for each supply station and the set (i.e., the totality) of the various transfer lines defines a delivery arrangement, which is often indicated by the technicians as "Day Set" or "Transfer Set". The closure according to the present disclosure may be advantageously used for directly connecting the container of the medical liquid with a transfer line of the delivery arrangement, thereby simplifying some preparatory steps for executing the injection as well as reducing some risks associated therewith. For instance, by using the closure of the present disclosure it is possible to avoid a specific and additional bottle connector which is typically used for connecting the bottle of a supply station to a transfer line, said bottle connector comprising a spike that pierces a rubber membrane of the bottle cap for accessing the liquid contained within the bottle. It is apparent that eliminating a component, as well as all the necessary operation steps needed for its connection, and, even more, avoiding the use of a piercing element, contributes in increasing the safety of the injector (for example, reducing the risk of environment contamination), in increasing the safety of the operator (who any longer does not run the risk of injuring himself) and in reducing the overall cost of a single injection procedure.

In any case, whatever it is, the injection system is typically provided with a connector 805 mating the connector 342 of the closure 135. For example, the connector 805 is a male luer lock fitting comprising a sleeve 810 that is provided with an internal thread matching the external thread possessed by the connector 342. The male luer lock fitting 805 further comprises a (tapered) connection conduit 815 housed within the sleeve 810, an outside surface of the connection conduit 815 matching an inside surface of the delivery conduit 339. The operator fits the connector 805 onto the connector 342 (i.e., the operator introduces a free end of the connection conduit 815 into a front part of the delivery conduit 339) and then s/he screws the connector 805 onto the connector 342 (alternatively, the operator screws the connector 342 onto the connector 805). As a result, the connector 805 rotationally slides (i.e., translates) into the closure 135 (downwards).

At this point, the operator rotates the closure 135 in the opposite direction with respect to the previously performed rotation (i.e., counterclockwise in the example at issue as indicted by the arrows); for this purpose, as above the operator acts on the cover 230, which drags the cap 205 that, in turn, drags the cursor 210 (whereas the insert 215 remains integral with the container 110). As a result, the cursor 210 unscrews from the insert 215, so as to translate downwards (inwards the closure 135). The valve member 424 then slides accordingly (downwards) along the delivery conduit 339. At this point of the operation, the valve member 424 is brought to an open position (see FIG. 8E), wherein the valve member 424 exits from the delivery conduit 339 thereby clearing the delivery port 336, so as to put the delivery conduit 339 in fluid communication with the interior of the container 110 through the delivery port 336. At the same time, the cursor suction conduit 433 as well slides accordingly (downwards) along the cap suction conduit 345, without leaving it (see FIG. 8F). As better visible in a corresponding enlarged portion of the cap 205 and the cursor 210, the closure 135 is rotated until a rear stop face of the teeth 418 of the tabs 415 of the cursor 210 abut against a rear stop face of the teeth 333 of the tabs 330 of the cap 205; this (opening) end-of-stroke position (see in FIG. 8E) is reached with a rotation (for example, from 2.0 to 3.0 turns, such as 2.6 turns) that is longer than the one required to reach the breaking end-of-stroke position (for example, with the first one equal to 1.1-2.5, preferably 1.2-2.0 and still more preferably 1.3-1.7, such as 1.5 time of the latter one).

Therefore, the use of the medical product requires two distinct operations; particularly, a (first) rotation is needed to break the frangible element and a (second) rotation is needed to open the delivery port. These two rotations are in opposite directions, so as to limit the risk of any accidental maneuver on the medical product. Moreover, the rotation for opening the delivery port is counterclockwise and then very intuitive; conversely, the rotation for breaking the frangible element is clockwise and then it requires an (extra-closure) operation done on purpose (so as to add further safety).

Figure 8E:
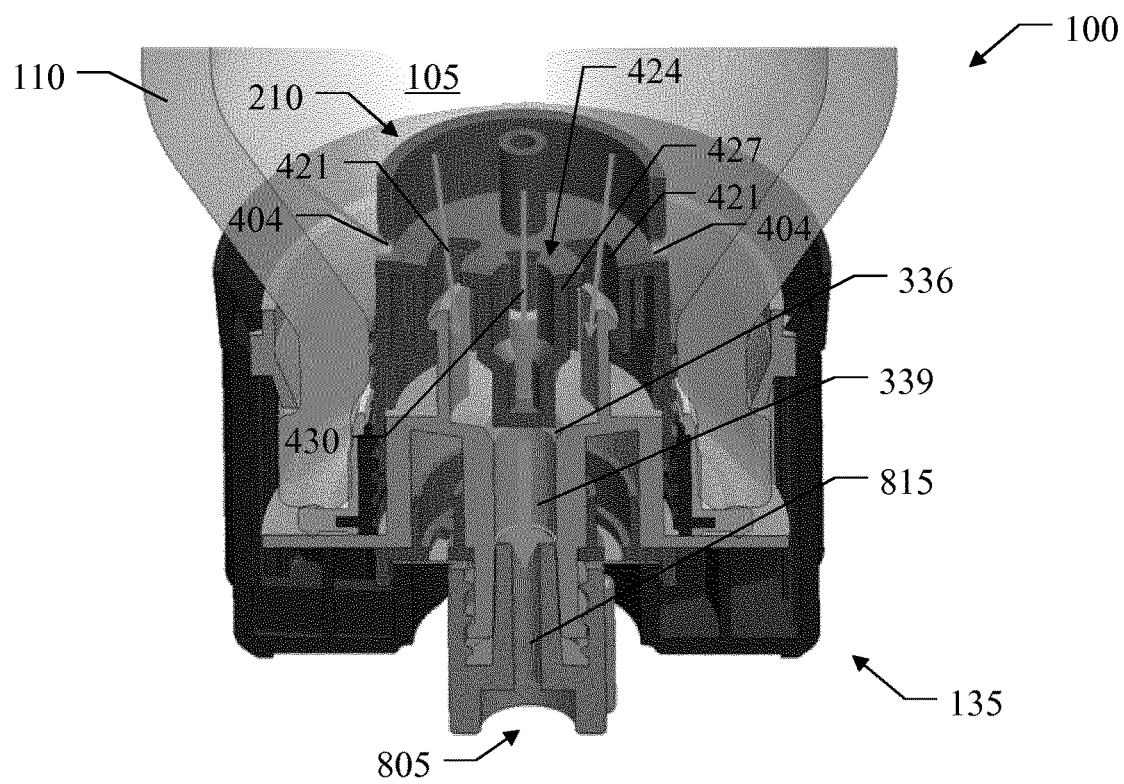

Moving to FIG. 8E, the operator overturns the medical product 100 in order to have the closure 135 facing downwards. In this condition, the medical liquid 105 flows from the container 110 into the cursor 210 (axially and laterally through its saddles 404), wherein it crosses the windows 421 and 430 of the cursor 210; the medical liquid 105 flows through the delivery port 336 into the delivery conduit 339 of the closure 135 and then into the connection conduit 815 of the connector 805. Moreover, the lateral windows 430 of the valve member 424 prevent (or at least substantially reduce) any buildup of the medical liquid 105 within the (hollow) turret 427.

Figure 8F:
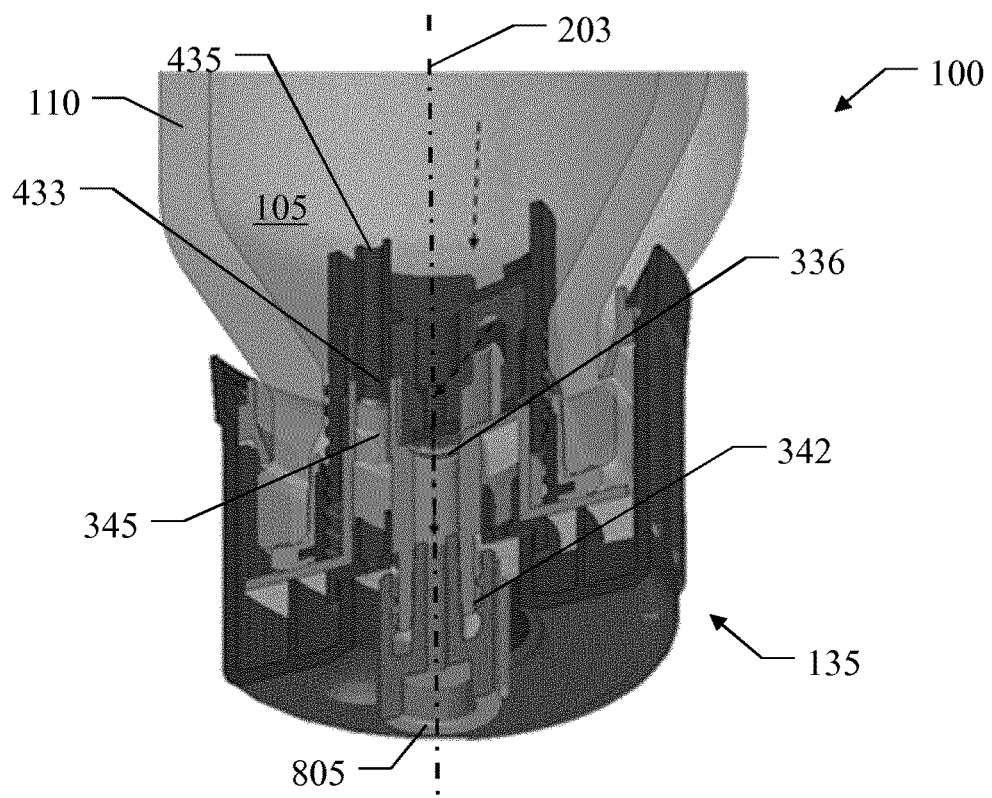

Moving to FIG. 8F, at the same time air is suctioned from the external environment through the cap suction conduit 345 and the cursor suction conduit 433, and then it enters the container 110 through the suction port 435. The air entering the container 110 compensates for the pressure reduction within the container 110 caused by the delivery of the medical liquid 105 (balancing an internal pressure in the container 110 with an atmospheric pressure outside it). Moreover, thanks to the design of the closure 135 (especially thanks to the fact that the delivery port 336 is spaced apart along the longitudinal axis 203 of the closure 135 from the suction port 435 by the length of cap suction conduit 345 plus the portion of the cursor suction conduit 433 projecting outside the cap suction conduit 345, i.e., the two ports are at different heights—different depths—inside the container 100), the air enters the container 110 far away from the delivery port 336 (from which the medical liquid 105 exits the container 110), so as to significantly limit any risk of mixing air bubbles with the medical liquid 105 that is delivered from the container.

Once the desired operation has been completed (for example, the container 110 has been emptied, or one or more injections associated with scan examinations have been completed), the operator unscrews the connector 805 from the connector 342 (either in this overturned condition or after the medical product 100 has been overturned again to have the closure 135 facing upwards).

Figure 8G:
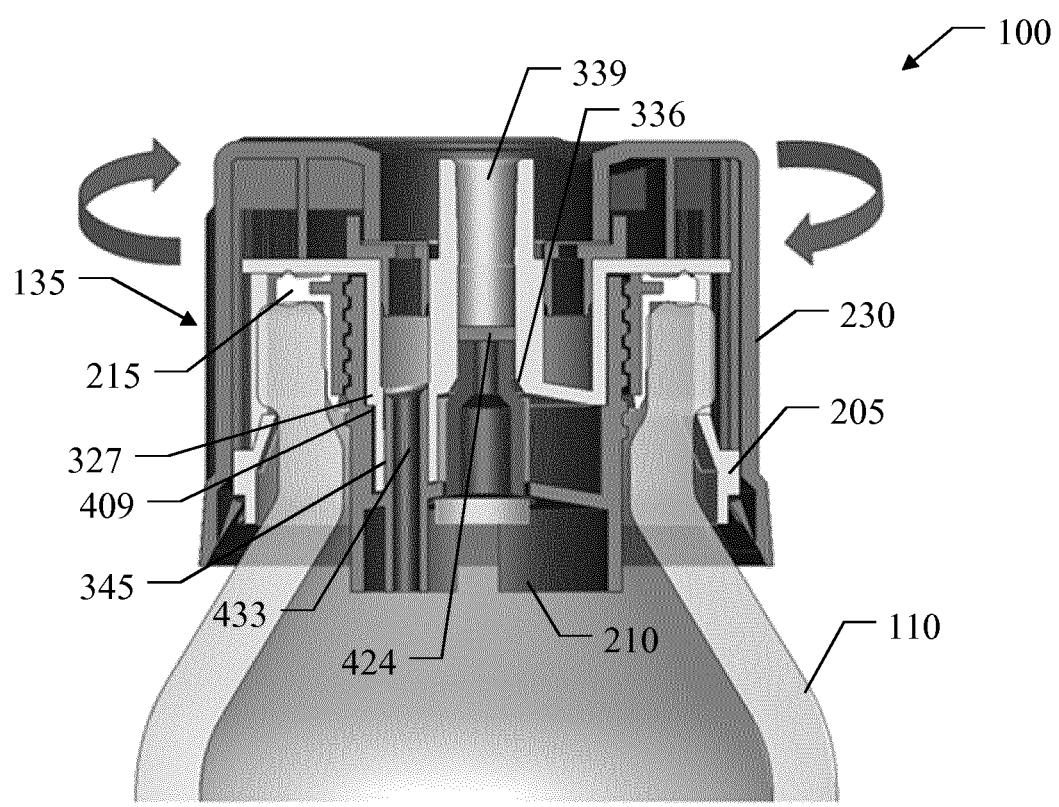

Moving to FIG. 8G, finally the operator overturns the medical product 100 again to have the closure 135 facing upwards (if not already done before). The operator then rotates the closure 135 in the opposite direction with respect to the last performed rotation (i.e., clockwise in the example at issue as indicated by the arrows), by acting onto the cover 230, which drags the cap 205 that, in turn, drags the cursor 210 (whereas the insert 215 remains integral with the container 110) that translates upwards (outwards the closure 135). The valve member 424 then slides accordingly (upwards) along the delivery conduit 339. In this way, as shown in the figure, the valve member 424 returns to the closed position, wherein the valve member 424 re-enters the delivery conduit 339 thereby sealing the delivery port 336 again, so as to prevent the dispersion of any medical liquid that may have remained inside the container 110. At the same time, the cursor suction conduit 433 as well slides accordingly (upwards) along the cap suction conduit 345 further entering therein. The closure 135 is rotated until the bottom walls of the grooves 409 of the cursor 210 abut against the axial free ends of the ribs 327 of the cap 205 again. The operator then disposes the (substantially empty) medical product 100 as usual.

Modifications

In order to satisfy local and specific requirements, a person skilled in the art may apply many logical and/or physical modifications and alterations to the present disclosure. More specifically, although this disclosure has been described with a certain degree of particularity with reference to one or more embodiments thereof, it should be understood that various omissions, substitutions and changes in the form and details as well as other embodiments are possible. Particularly, different embodiments of the present disclosure may even be practiced without the specific details (such as the numerical values) set forth in the preceding description to provide a more thorough understanding thereof; conversely, well-known features may have been omitted or simplified in order not to obscure the description with unnecessary particulars. Moreover, it is expressly intended that specific elements and/or method steps described in connection with any embodiment of the present disclosure may be incorporated in any other embodiment as a matter of general design choice. In any case, each numerical value should be read as modified by the term about (unless already done) and each range of numerical values should be intended as expressly specifying any possible number along the continuum within the range (comprising its end points). Moreover, ordinal or other qualifiers are merely used as labels to distinguish elements with the same name but do not by themselves connote any priority, precedence or order. The terms include, comprise, have, contain and involve (and any forms thereof) should be intended with an open, non-exhaustive meaning (i.e., not limited to the recited items); the terms based on, dependent on, according to, function of (and any forms thereof) should be intended as a non-exclusive relationship (i.e., with possible further variables involved); the term a/an should be intended as one or more items (unless expressly indicated otherwise); and the term means for (or any means-plus-function formulation) should be intended as any structure adapted or configured for carrying out the relevant function.

For example, an embodiment provides a closure for closing a mouth of a container of a liquid. However, the closure may be of any type, shape, size and material (for example, transparent to shown the condition of the frangible element), and it may be used with any container of any liquid (see below).

In an embodiment, the closure comprises a cap. However, the cap may be of any type, shape, size and material.

In an embodiment, the cap has fixing means for fixing the cap to the container. However, the fixing means may be implemented with any structure (for example, in addition to the above-described teeth of the cap, of any other snap-fitting type, of screwing type).

In an embodiment, the cap is rotatable around a longitudinal axis of the container (in a fixed condition wherein the closure is fixed to the container). However, the cap may be rotated in any way (for example, by acting on the cap through the cover as described above, through any other element or even directly).

In an embodiment, the cap has a delivery port for delivering the liquid from the container. However, the delivery port may be of any shape, size and it may be provided at any suitable position within the closure.

In an embodiment, the cap has a cap suction conduit for suctioning air into the container during the delivering of the liquid. However, the cap suction conduit may be of any shape, size and it may be provided at any suitable position within the closure.

In an embodiment, the cap has a connector for connecting to a delivery device of the liquid, which connector is in fluid communication with the delivery port. However, the connector may be of any type, shape, size and at any position (for example, of locking or fitting type, male or female), for connecting to any delivery device (for example, of an injection system or a syringe) in any way (for example, by screwing, snap-fitting the delivery device and/or the connector); moreover, the connector may be in fluid communication with the delivery port in any way (for example, via the delivery conduit as described above, via any other element or even directly).

In an embodiment, the closure comprises a cursor. However, the cursor may be of any type, shape, size and material.

In an embodiment, the cursor has a thread for screwing the cursor with respect to the container. However, the thread may be of any type, shape, size and at any position (for example, extending along any part of the cursor up to its entirety); moreover, this thread may be used for screwing the cursor with respect to the container in any way (for example, through any insert or even directly when the container is already provided with a corresponding thread).

In an embodiment, the cursor has a valve member in a closed position wherein the valve member closes the delivery port. However, the valve member may be of any type, shape and size (for example, a tube, a disc, a ball) and it may close the delivery port in any way (for example, arranged within the delivery conduit or even outside it at the delivery port).

In an embodiment, the cursor has a cursor suction conduit that is slidebly coupled with the cap suction conduit. However, the cursor suction conduit may be of any shape, size and at any position (for example, with the cursor suction conduit that is shortened by moving the frangible element inwards the container, maintaining a length enough to drive the sliding of the cursor suction conduit, or it is lengthened by moving the frangible element outwards the container, without reaching a length wherein the cursor suction conduit reaches the holder of the filter); moreover, the cursor suction conduit may slide with respect to the cap suction conduit in any way (for example, internally as described above or externally should the frangible element be provided in the cursor suction conduit) and to any extent (up to completely, always or only in use).

In an embodiment, the closure comprises a frangible element closing the cap suction conduit or the cursor suction conduit. However, the frangible element may be of any type, shape, size and material (for example, a membrane, a septum, a thin wall, with or without any feature for facilitating its breaking, such as pre-cut lines extending in any direction, like circumferentially or radially, and/or thinner portions); moreover, the frangible element may be at any position (for example, in the cap suction conduit as described above or in the cursor suction conduit if the cap suction conduit slides inside it, at any position in the corresponding suction conduit, either within it or at its border, with the other suction conduit at any distance thereof).

In an embodiment, the closure comprises dragging means for dragging the cursor into rotation by the cap. However, the dragging means may be implemented with any structure (for example, in addition to the above-described ribs of the cap and grooves of the cursor, by inverting them, by interlocked teeth, staggered ribs).

In an embodiment, the closure is configured to cause the cursor to slide with respect to the cap in response to at least one rotation of the cap. However, the cursor may slide to any extent and in any direction in response to any number, length and type of rotations (for example, sliding inwards/outwards in response to one or more clockwise/counterclockwise rotations).

In an embodiment, as a result of said at least one rotation of the cap the cursor suction conduit moves to break the frangible element (putting in fluid communication the cursor suction conduit with the cap suction conduit), and the valve member moves to an open position (wherein the valve member opens the delivery port). However, the frangible element may be broken in any way (for example, centrally, laterally), the delivery port may be opened in any way (for example, by the valve member that clears the delivery port or simply exposes one or more windows provided laterally therein); moreover, these results may be obtained with two rotations in different directions (to increase the safety) or with a single rotation, either at the same time or in two steps (to speed up the operation in emergency situations), and additional operations may be performed at the same time (for example, breaking a further frangible element closing the delivery port).

In an embodiment, the closure is configured to cause the cursor to slide with respect to the cap in response to a further rotation of the cap, thereby moving the valve member to a further closed position (wherein the valve member closes the delivery port). However, the delivery port may be closed in any way (with the further closed position that is either the same or different with respect to the closed position); moreover, this result may be obtained with any rotation (for example, with any extent and/or direction). In any case, the possibility is not excluded of preventing the closure of the container, in order to avoid any further use thereof so that each container is used for one single patient only and it may not be re-used for more patients (for example, with the cap that may be rotated only in one direction both to break the frangible element and to open the delivery port).

In an embodiment, the closure is configured to cause the cursor to slide outwards the container in the fixed condition in response to a first rotation in a first direction (of said at least one rotation of the cap), thereby moving the cursor suction conduit to break the frangible element; moreover, the closure is configured to cause the cursor to slide inwards the container in the fixed condition in response to a second rotation in a second direction opposite the first direction (of said at least one rotation of the cap) thereby moving the valve member to the open position. However, the slidings and the rotations may have any extent and they may be of any type (for example, with the cursor that slides outwards and inwards when the cap is rotated clockwise and counterclockwise, respectively, or vice-versa).

In an embodiment, the first rotation is shorter than the second rotation. However, the two rotations may have any length, either in relative terms or in absolute terms (with the first rotation that may be shorter than, equal to or higher than the second rotation).

In an embodiment, the closure comprises an insert for press-fitting into the container. However, the insert may be of any type, shape, size and material; moreover, the insert may be fixed to the container in any way (for example, glued, welded in addition and/or in alternative to be press-fitted).

In an embodiment, the insert has an internal thread matching the thread of the cursor (with the thread of the cursor that is an external thread screwed into the internal thread). However, the two threads may be of any type, shape, size and at any position; moreover, the possibility is not excluded of inverting the threads (i.e., with the internal thread on the cursor and the external thread on the insert or the container).

In an embodiment, the insert comprises an internal portion of a first material (having the internal thread) and an external portion of a second material (implementing a gasket for sealing the mouth). However, the two portions may be of any material and they may be joined in any way (for example, welded, glued in addition or in alternative to the above-described overmolding); in any case, the possibility is not excluded of making the insert from a single material or of providing two distinct elements (i.e., a bush and a gasket).

In an embodiment, the external portion of the insert comprises a hollow cylindrical body (for press-fitting into the container) and a flange (for remaining outside the container in the fixed condition). However, the hollow cylindrical body and the flange may have any size and shape; more generally, the external portion may have any other structure for acting within the mouth and/or at its edge (for example, only a cylinder, only a ring, a cylinder and a distinct ring).

In an embodiment, the flange has a protruding structure for reducing a contact surface with the cap. However, the protruding structure may reduce the contact surface in any way and to any extent (for example, continually around the whole flange or only at specific spots), and it may be implemented in any way (for example, with any number of the above-described bulging rings, or more generally with any other protruding elements, such as bumps, and/or depressions).

In an embodiment, the fixing means are for fixing the cap to the container in a non-removable way. However, this result may be achieved in any way (for example, with any snap-fitting structure, such as with any number of teeth, with an external fastener, such as a band); in any way, the possibility is not excluded of having the cap removable (more or less easily).

In an embodiment, the closure comprises a cover that is fixed in a non-removable way to the cap. However, the cover may be of any type, shape, size, material and it may be fixed to the cap in any way (either the same or different with respect to the fixing of the cap to the container, even in a removable way); in any case, the cover may also be omitted at all.

In an embodiment, the cover prevents access to the fixing means (in the fixed condition). However, the cover may have any function (comprising a mere aesthetic one).

In an embodiment, the closure comprises further dragging means for dragging the cap into rotation by the cover. However, the further dragging means may be implemented with any structure, either the same or different with respect to the dragging means (for example, in addition to the above-described staggered ribs, by ribs and grooves, interlocked teeth).

In an embodiment, the closure comprises a filter for filtering the air that is suctioned through the cap suction conduit. However, the filter may be of any type (for example, one or more membranes or spongy layers for filtering bacteria, other microorganisms, dust) and it may be of any shape, size and at any position (for example, with or without any holder, smaller than, equal to or larger than a cross-section of the cap suction port). In any case, the possibility is not excluded of omitting the filter at all.

In an embodiment, the filter is fixed between the cap and the closure. However, the filter may be fixed in any way between the cap and the closure (for example, by the interference of any number and type of elements thereof, acting in any way on the holder of the filter and/or directly on it), or more generally in any other way (for example, press-fitted, glued, welded in addition and/or in alternative to be enclosed between any pair of components of the cover).

In an embodiment, the cursor suction conduit has a suction port at an end thereof opposite the cap suction conduit. However, the suction port may have any shape and size, and it may be arranged at any position within the container (for example, facing inwards or laterally).

In an embodiment, the suction port and the delivery port are spaced apart along the longitudinal axis of the closure when the valve member is in the open position. However, the delivery port and the suction port may be at any relative position (for example, with the delivery port more internal or more external than the suction port with respect to the container in the fixed condition of the closure); in any case, the delivery port and the suction port may be at any distance longitudinally (for example, given by the length of the cap suction conduit and/or the portion of the cursor suction conduit projecting outside the cap suction conduit), down to zero.

In an embodiment, the valve member comprises a hollow turret that has one or more lateral windows. However, the hollow turret may be of any size and shape (for example, squared) and the windows may be in any number, of any shape, size and at any position; in any case, these windows may also be omitted at all (for example, in case of a solid turret).

In an embodiment, the closure comprises stopping means for preventing the cursor to leave the cap when the valve member is in the open position. However, the stopping means may be implemented with any structure (for example, in addition to the above-described interlocking teeth, by latches or broken threads) or they may be omitted at all (for example, by limiting the corresponding rotation of the cap).

In an embodiment, the cursor suction conduit ends with a sharpened tip facing the cap suction conduit for facilitating the breaking of the frangible element. However, the sharpened tip may be of any type (for example, a slanted end or a needle); in any case, the cursor suction conduit may end with any other shape.

In an embodiment, the closure has a through-hole that exposes the connector and the cap suction conduit. However, the through-hole may be of any shape, size and at any position (for example, with or without any access dips).

In an embodiment, the closure comprises a press-fitting lid closing the through-hole. However, the lid may be of any shape, size, material, and it may be fixed in any way (for example, by snap fitting or screwing); in any case, the lid may also be used to close the container after use or it may be omitted at all.

In an embodiment, the closure comprises a peelable protection film that seals the through-hole (closed by the lid). However, the protection film may be of any shape, size, material (for example, with or without the handling tab), and it may be fixed in any way (for example, welded or glued); in any case, the protection film may also be omitted at all (either alone or together with the lid).

An embodiment provides a product that comprises a container containing a liquid and the above-mentioned closure fixed to the container (to close a mouth thereof). However, the product may be of any type (for example, for medical or non-medical applications). The container may be of any type (for example, a bottle, a vial or any other container with a rigid mouth) and of any size, shape and material (for example, glass, plastic); the container may contain any amount and type of liquid (for example, in medical applications for diagnostic or therapeutic purposes, the liquid may be a contrast agent, a saline solution, a drug, or more generally in non-medical applications for any other purpose, the liquid may be polish, enamel, varnish, dye).

Generally, similar considerations apply if the closure and the product comprising it each one has a different structure or comprises equivalent components (for example, of different materials), or it has other operative characteristics. In any case, every component thereof may be separated into more elements, or two or more components may be combined together into a single element; moreover, each component may be replicated to support the execution of the corresponding operations in parallel. Moreover, unless specified otherwise, any interaction between different components generally does not need to be continuous, and it may be either direct or indirect through one or more intermediaries.

An embodiment provides a method for using the above-mentioned product, which method comprises applying at least one rotation to the cap to cause the cursor to slide with respect to the cap, thereby moving the cursor suction conduit to break the frangible element (putting in fluid communication the cursor suction conduit with the cap suction conduit) and moving the valve member to the open position (wherein the valve member opens the delivery port wherein the valve member opens the delivery port).

In an embodiment, the method comprises applying a further rotation to the cap to cause the cursor to slide with respect to the cap thereby moving the valve member to a further closed position (wherein the valve member closes the delivery port).

An embodiment provides a method for assembling the above-mentioned closure, which method comprises mounting the cursor into the cap. However, the result may be achieved in different ways (for example, by mounting the holder with the filter into the cap and/or by mounting the cover onto the cap before mounting the cursor into the cap).

An embodiment provides a method for manufacturing the above-mentioned product, which method comprises filling the container with the liquid and then mounting the closure onto the container.

Generally, similar considerations apply if the same solution is implemented with equivalent methods (by using similar steps with the same functions of more steps or portions thereof, removing some steps being non-essential, or adding further optional steps); moreover, the steps may be performed in a different order, concurrently or in an interleaved way (at least in part).

The invention claimed is:

1. A closure (135) for closing a mouth (125) of a container (110) of a liquid (105), the closure (135) comprising:
   a cap (205) having fixing means (318) for fixing the cap (205) to the container (110), the cap (205) being rotatable around a longitudinal axis (203) of the container (110) in a fixed condition wherein the closure (135) is fixed to the container (110), a delivery port (336) for delivering the liquid (105) from the container (110), a cap suction conduit (345) for suctioning air into the container (110) during the delivering of the liquid (105) and a connector (342) for connecting a delivery device (805) of the liquid (105), the connector (342) being in fluid communication with the delivery port (336),
   a cursor (210) having a thread (406) for screwing the cursor (205) with respect to the container (110), a valve member (424) in a closed position wherein the valve member (215) closes the delivery port (336), and a cursor suction conduit (433) slidebly coupled with the cap suction conduit (345),
   a frangible element (351) closing the cap suction conduit (345) or the cursor suction conduit (433), and
   dragging means (327,409) for dragging the cursor (210) into rotation by the cap (205), wherein the closure (135) is configured to cause the cursor (210) to slide with respect to the cap (205) in response to at least one rotation of the cap (205) thereby moving the cursor suction conduit (433) to break the frangible element (351), putting in fluid communication the cursor suction conduit (433) with the cap suction conduit (345), and moving the valve member (424) to an open position, wherein the valve member (215) opens the delivery port (336).

2. The closure (135) according to claim 1, wherein the closure (135) is configured to cause the cursor (210) to slide with respect to the cap (205) in response to a further rotation of the cap (205) thereby moving the valve member (424) to a further closed position, wherein the valve member (215) closes the delivery port (336).

3. The closure (135) according to claim 1, wherein the closure (135) is configured to cause the cursor (210) to slide outwards the container (110) in the fixed condition in response to a first rotation in a first direction of said at least one rotation of the cap (205) thereby moving the cursor suction conduit (433) to break the frangible element (351) and to cause the cursor (210) to slide inwards the container (110) in the fixed condition in response to a second rotation in a second direction opposite the first direction of said at least one rotation of the cap (205) thereby moving the valve member (424) to the open position.

4. The closure (135) according to claim 3, wherein the first rotation is shorter than the second rotation.

5. The closure (135) according to claim 1, wherein the closure (135) comprises an insert (215) for press-fitting into the container (110) having an internal thread (454) matching the thread (406) of the cursor (210), the thread (406) of the cursor (210) being an external thread (406) screwed into the internal thread (454).

6. The closure (135) according to claim 5, wherein the insert (215) comprises an internal portion (448) of a first material having the internal thread (454) and an external portion (436) of a second material implementing a gasket for sealing the mouth (125).

7. The closure (135) according to claim 6, wherein the external portion (436) of the insert (215) comprises a hollow cylindrical body (439) for press-fitting into the container (110) and a flange (442) for remaining outside the container (110) in the fixed condition, the flange (442) having a protruding structure (445) for reducing a contact surface with the cap (205).

8. The closure (135) according to claim 1, wherein the fixing means (318) are for fixing the cap (205) to the container (110) in a non-removable way and wherein the closure (135) comprises a cover (230) fixed in a non-removable way to the cap (205), the cover (230) preventing access to the fixing means (318) in the fixed condition, and further dragging means (324,535) for dragging the cap (205) into rotation by the cover (230).

9. The closure (135) according to claim 8, wherein the closure (135) comprises a filter (220) for filtering the air being suctioned through the cap suction conduit (345), the filter (220) being fixed between the cap (205) and the closure (230).

10. The closure (135) according to claim 1, wherein the cursor suction conduit (433) has a suction port (434) at an end thereof opposite the cap suction conduit (345), the suction port (434) and the delivery port (336) being spaced apart along the longitudinal axis (203) of the closure (135) when the valve member (424) is in the open position.

11. The closure (135) according to claim 1, wherein the valve member (424) comprises a hollow turret (427) having one or more lateral windows (430).

12. The closure (135) according to claim 1, wherein the closure (135) comprises stopping means (333,418) for preventing the cursor (210) to leave the cap (205) when the valve member (424) is in the open position.

13. The closure (135) according to claim 1, wherein the cursor suction conduit (433) ends with a sharpened tip (435) facing the cap suction conduit (345) for facilitating the breaking of the frangible element (351).

14. The closure (135) according to claim 1, wherein the closure (135) has a through-hole (515) exposing the connector (342) and the cap suction conduit (345), the closure (135) comprising a press-fitting lid (235) closing the through-hole (515) and a peelable protection film (240) sealing the through-hole (515) being closed by the lid (235).

15. A product (100) comprising a container (110) containing a liquid (105) and the closure (135) according to claim 1 fixed to the container (110) to close a mouth (125) thereof.

* * * * *